(12) United States Patent
Bigot et al.

(10) Patent No.: US 11,191,444 B2
(45) Date of Patent: Dec. 7, 2021

(54) PROCESSING SYSTEM AND DYNAMIC CORRECTION METHOD FOR THERMAL THERAPY

(71) Applicant: Profound Medical Inc., Mississauga (CA)

(72) Inventors: Alexandre Bigot, Toronto (CA); Patrick Leonard, Toronto (CA)

(73) Assignee: Profound Medical Inc., Mississauga (CA)

( * ) Notice: Subject to any disclaimer, the term of this patent is extended or adjusted under 35 U.S.C. 154(b) by 341 days.

(21) Appl. No.: 15/788,414

(22) Filed: Oct. 19, 2017

(65) Prior Publication Data

US 2019/0117108 A1 Apr. 25, 2019

(51) Int. Cl.
| | |
|---|---|
| *A61B 5/055* | (2006.01) |
| *A61B 5/00* | (2006.01) |
| *A61B 5/01* | (2006.01) |
| *A61N 7/02* | (2006.01) |
| *A61N 7/00* | (2006.01) |
| *A61B 34/10* | (2016.01) |
| *G01R 33/48* | (2006.01) |
| *A61B 90/00* | (2016.01) |

(52) U.S. Cl.
CPC ............. *A61B 5/055* (2013.01); *A61B 5/015* (2013.01); *A61B 5/4836* (2013.01); *A61B 34/10* (2016.02); *A61N 7/00* (2013.01); *A61N 7/02* (2013.01); *G01R 33/4804* (2013.01); *G01R 33/4808* (2013.01); *A61B 2090/374* (2016.02); *A61N 2007/0043* (2013.01)

(58) Field of Classification Search
CPC ....... A61B 5/015; A61B 5/055; A61B 5/4836; A61N 7/02; G01R 33/4804; G01R 33/4808
See application file for complete search history.

(56) References Cited

U.S. PATENT DOCUMENTS

2004/0010191 A1* 1/2004 Yatsui .................. A61B 5/4872
600/410
2007/0230757 A1 10/2007 Trachtenberg et al.
(Continued)

FOREIGN PATENT DOCUMENTS

JP 11253420 A 9/1999
JP 2000000224 A 1/2000
(Continued)

OTHER PUBLICATIONS

Maier et al. (Robust Phase Unwrapping for MR Temperature Imaging using a Magnitude-sorted List, Multi-clustering Algorithm-Magn Reson Med. Apr. 2015 ; 73(4): 1662-1668) (Year: 2015).*
Roujol, S. et al., "Real-Time MR-Thermometry and Dosimetry for Interventional Guidance on Abdominal Organs", Magnetic Resonance in Medicine, Mar. 29, 2010, pp. 1080-1087, vol. 63, Issue 4.
Agnello, L. et al., "Smart Techniques for Fast Medical Image Analysis and Processing", Doctoral Thesis, Dec. 31, 2015, Chapter 2: Sections 2.3, 2.4, and Chapter 5, University of Palermo.
(Continued)

*Primary Examiner* — Joanne M Hoffman
*Assistant Examiner* — Alexei Bykhovski
(74) *Attorney, Agent, or Firm* — Intrinsic Law Corp.

(57) ABSTRACT

In one aspect, a method comprises: receiving data indicative of at least one phase image captured using a magnetic resonance imaging (MRI) device during delivery of thermal therapy by a thermal therapy applicator to a target volume within a patient's body; and processing said at least one phase image; wherein said processing said at least one phase image comprises: applying a first mask; applying phase unwrap; and applying a second mask.

22 Claims, 28 Drawing Sheets

(56) References Cited

U.S. PATENT DOCUMENTS

| | | | |
|---|---|---|---|
| 2007/0239062 A1* | 10/2007 | Chopra | A61B 5/4381 600/549 |
| 2009/0118610 A1* | 5/2009 | Karmarkar | A61B 5/0476 600/420 |
| 2010/0286517 A1* | 11/2010 | Kamen | A61B 10/0241 600/438 |
| 2011/0206250 A1* | 8/2011 | McGinnis | G06T 7/0012 382/128 |
| 2012/0070058 A1 | 3/2012 | Raju et al. | |
| 2015/0080705 A1* | 3/2015 | Partanen | A61N 7/02 600/411 |
| 2015/0087963 A1* | 3/2015 | Tyc | A61B 18/22 600/411 |
| 2015/0258353 A1 | 9/2015 | Partanen et al. | |
| 2017/0059682 A1 | 3/2017 | Dagher | |

FOREIGN PATENT DOCUMENTS

| | | |
|---|---|---|
| JP | 2006223877 A | 8/2006 |
| JP | 2011182983 A | 9/2011 |
| JP | 2015512284 A | 4/2015 |

OTHER PUBLICATIONS

Rieke, V. et al., "MR Thermometry", Journal of Magnetic Resonance Imaging, Jan. 24, 2008, pp. 376-390, vol. 27, Issue 2.
ISA, "International Search Report", PCT/IB2017/001506, dated Jul. 16, 2018.
JPO, "Office Action", JP 2020-522012, dated Jun. 30, 2021.

\* cited by examiner

| MASK | BASED ON | TYPE | IDENTICAL ON ALL SLICES | CONDITION | EXAMPLE |
|---|---|---|---|---|---|
| UA MASK | UA CENTER | EXCLUSIVE | YES | EXCLUDE PIXELS FARTHER THAN 40 mm FROM THE UA CENTER | |
| RECTUM MASK | UA CENTER | EXCLUSIVE | YES | EXCLUDE PIXELS BELOW THE UA CENTER (Y-DIRECTION), AND FARTHER THAN 30 mm FROM THE UA X-COORDINATE | |
| PROSTATE MASK | PROSTATE CONTOUR | INCLUSIVE | NO | INCLUDE ANY PIXEL WHOSE CENTER IS CONTAINED WITHIN THE CONTOUR | |

STATIC MASKS

| MASK | BASED ON | TYPE | IDENTICAL ON ALL SLICES | CONDITION | EXAMPLE |
|---|---|---|---|---|---|
| STABILITY MASK | TEMPERATURE VARIATIONS | INCLUSIVE AND CUMULATIVE | NO | INCLUDE ALL PIXELS WHOSE TEMPERATURE VARIATION BETWEEN TWO DYNAMICS IS LESS THAN 10 DEGREES C | |
| SNR MASK | MAGNITUDE IMAGE | INCLUSIVE AND CUMULATIVE | NO | BASED ON OSTU'S METHOD, KEEP ALL PIXELS BELOW OSTU'S THRESHOLD | |
| SECTOR MASK | CURRENT BEAM POSITIONS | INCLUSIVE | NO | CONDITION BASED ON CURRENT BEAM ANGLE, PROSTATE CONTOUR AND UA CENTER | |

DYNAMIC MASKS 1200

FIG. 12

| CORRECTION | MASK(S) USED | BASED ON | MASKED IMAGE EXAMPLE |
|---|---|---|---|
| DRIFT CORRECTION | UA MASK & RECTUM MASK & STABILITY MASK & SNR MASK | PHASE IMAGE |  |
| PHASE UNWRAP | NONE | PHASE IMAGE |  |
| TEMPERATURE CORRECTIONS | NONE | PHASE IMAGE | 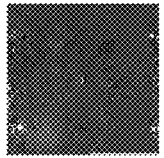 |
| SPATIAL CO-REGISTRATION | NONE | MAGNITUDE IMAGE |  |
| BOILING DETECTION SHUTOFF | SECTOR MASK | TEMPERATURE IMAGE | 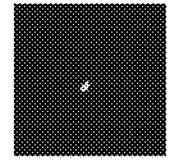 |
FIG. 14

PROCESSING SYSTEM AND DYNAMIC CORRECTION METHOD FOR THERMAL THERAPY

TECHNICAL FIELD

The present application relates to thermal therapy and/or other systems and methods that use temperature measurements derived from magnetic resonance imaging (MRI).

BACKGROUND

The use of magnetic resonance imaging (MRI) to obtain temperature related data in a tissue ablation procedure is discussed, e.g., in U.S. Pat. No. 7,771,418, which is hereby incorporated by reference in its entirety. One application for such therapies is in treating a diseased male prostate.

Temperature measurements derived from MRI methods are subject to errors or potential errors from a variety of sources. These errors or potential errors can create temperature measurement uncertainty and/or significantly reduce the accuracy of measuring temperature changes.

When temperature measurements are used as part of a feedback system for thermal energy delivery, temperature measurement uncertainty and/or reduced accuracy can make it more difficult to determine whether there has been a lack of heating in a target region and/or unintended heating of any other regions. Lack of heating in a target region can result in an incomplete thermal therapy session. Unintended heating of other regions may require that thermal therapy be halted, at least temporarily, in order to allow such regions to cool. This can result in a less than optimal thermal therapy session from a patient comfort perspective, as well as less economical use of the MRI-thermal therapy facility, personnel and equipment.

Methods to address temperature measurement uncertainties are disclosed in U.S. Patent Application Publication No. 2015/0038883, filed on Aug. 4, 2014, entitled "Treatment Planning and Delivery Using Temperature Uncertainty Maps", which is hereby incorporated by reference in its entirety. One method disclosed therein reduces the magnitude of temperature measurement uncertainty by detecting drift in temperature measurements, and adjusting all temperatures measurements based on the detected drift.

SUMMARY

It has been determined that it is possible to further reduce the effects of errors and/or potential errors in systems and methods that use temperature measurements derived from magnetic resonance imaging (MRI).

At least some aspects disclosed herein have the ability to address noise from various sources, including: magnetic resonance (MR) artifacts, frequency drift, low SNR regions, non-uniform tissue structures and/or others.

Accordingly, improved accuracy and/or efficiency of delivery of MRI-guided thermal therapies and/or other systems and methods is made possible.

At least some aspects disclosed herein employ one or more dynamic correction methodologies during thermal treatment or other procedure, since noise levels can change over time.

In one aspect, a method comprises: receiving data indicative of at least one phase image captured using a magnetic resonance imaging (MRI) device during delivery of thermal therapy by a thermal therapy applicator to a target volume within a patient's body; and processing said at least one phase image; wherein said processing said at least one phase image comprises: applying a first mask; applying phase unwrap; and applying a second mask.

In at least some embodiments, the first mask and the second mask each provide diminishment and/or enhancement of one or more pixels in a phase (or other) image relative to one or more other pixels in the phase (or other) image, sometimes referred to herein as subjugation of one or more pixels in a phase (or other) image.

In at least some embodiments, the first mask and the second mask can each be categorized as either: (1) a static mask, which may be defined before treatment begins, based on user-defined landmarks or otherwise, and is not expected to change during treatment or (2) a dynamic mask, which may be computed or otherwise determined for every dynamic (or otherwise) during treatment, and may change during treatment.

In at least some embodiments, the method further comprises determining a treatment plan based at least in part on the processed at least one phase image; and delivering thermal therapy to the target volume within the patient's body based at least in part on said treatment plan using a thermal therapy applicator.

In at least some embodiments, said applying phase unwrap comprises: applying said phase unwrap between said applying a first mask and said applying a second mask.

In at least some embodiments, said thermal therapy comprises ultrasound thermal therapy; and said thermal therapy applicator comprises an ultrasound thermal therapy applicator.

In at least some embodiments, said first mask is a static mask and said second mask is a dynamic mask.

In at least some embodiments, said first mask and/or said second mask comprises a therapy applicator mask.

In at least some embodiments, said therapy applicator mask is an ultrasonic applicator mask In at least some embodiments, said first mask and/or said second mask comprises a target region mask.

In at least some embodiments, said target region mask is a prostate mask.

In at least some embodiments, said first mask and/or said second mask comprises a restricted region mask.

In at least some embodiments, said restricted region mask is a rectum mask.

In at least some embodiments, said first mask and/or said second mask comprises a dynamic mask and wherein said dynamic mask comprises a sector mask.

In at least some embodiments, said first mask and/or said second mask comprises a dynamic mask and wherein said dynamic mask comprises a noise mask.

In another aspect, a system comprises at least one computer hardware processor configured to perform the method.

In another aspect, at least one non-transitory computer readable storage medium stores processor-executable instructions that, when executed by at least one processor, result in the method.

This Summary is intended to provide an overview of at least some of the subject matter of the present patent application. It is not intended to provide an exclusive or exhaustive explanation of the invention or embodiments thereof. Further limitations and disadvantages of conventional and traditional approaches will become apparent to one of skill in the art, through comparison of such systems with some aspects of the present invention as set forth in the remainder of the present application with reference to the drawings.

However, while various features and/or advantages are described in this Summary and/or will become apparent in view of the following detailed description and accompanying drawings, it should be understood that such features and/or advantages are not required in all aspects and embodiments.

Moreover, this Summary is not exhaustive of the scope of the present aspects and embodiments. Thus, while certain aspects and embodiments have been presented and/or outlined in this Summary, it should be understood that the present aspects and embodiments are not limited to the aspects and embodiments in this Summary. Indeed, other aspects and embodiments, which may be similar to and/or different from, the aspects and embodiments presented in this Summary, will be apparent from the description, illustrations and/or claims, which follow.

Any aspects and/or embodiments that are described in this Summary and do not appear in the claims that follow are preserved for later presentation in this application or in one or more continuation patent applications. Any aspects and/or embodiments that are not described in this Summary and do not appear in the claims that follow are also preserved for later presentation or in one or more continuation patent applications.

IN THE DRAWINGS

Reference is made to the following detailed description in connection with the accompanying drawings, in which.

Figure 11A:
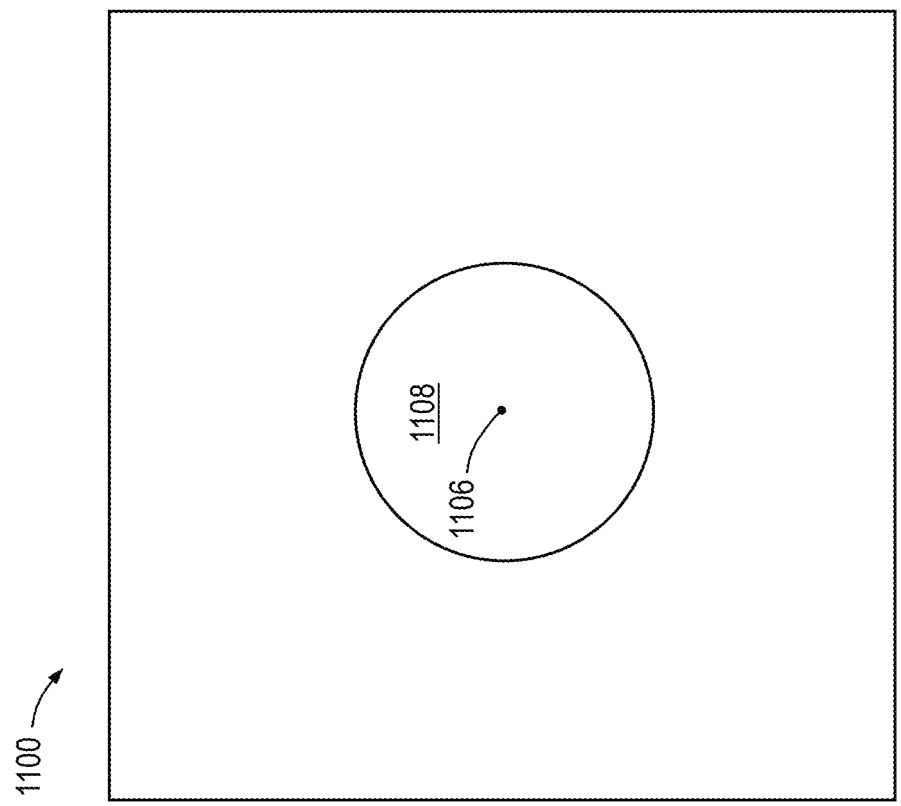
Figure 11B:
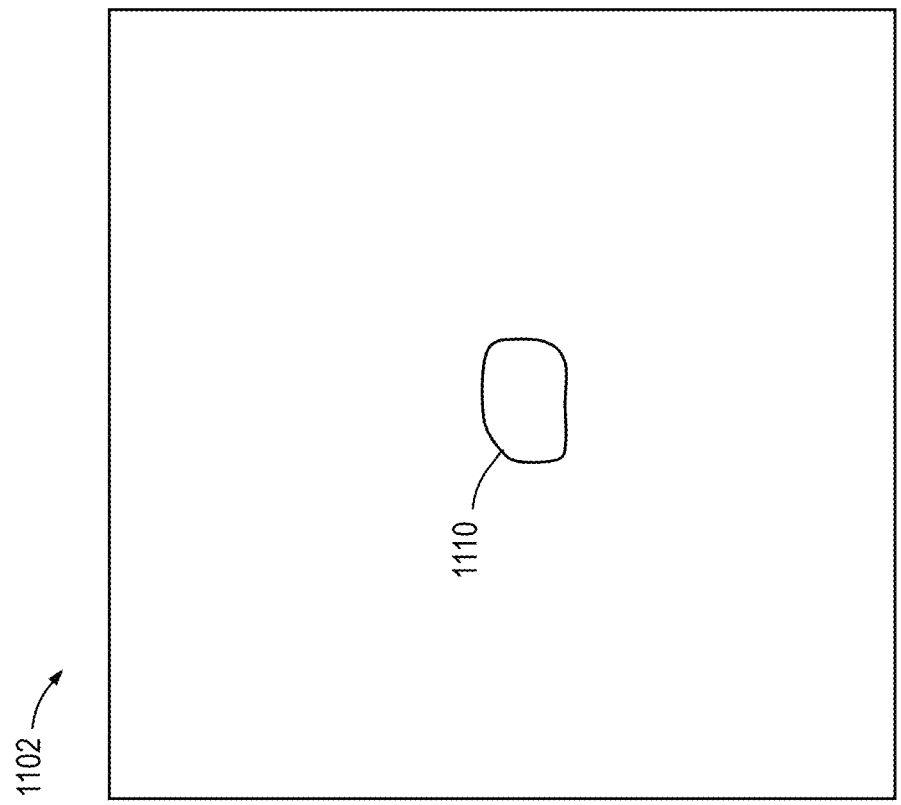
Figure 11C:
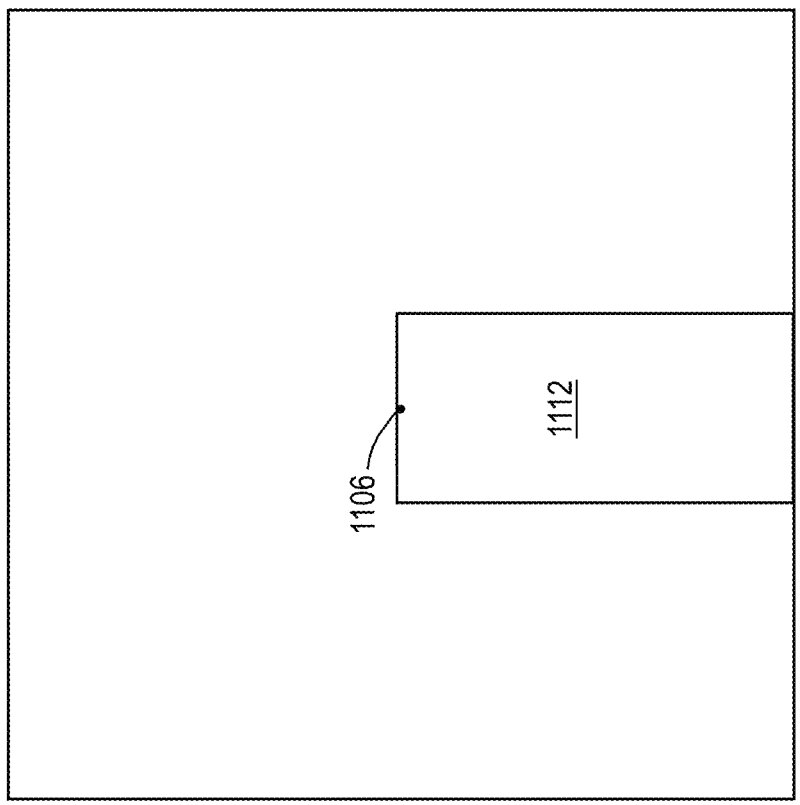
Figure 13A:
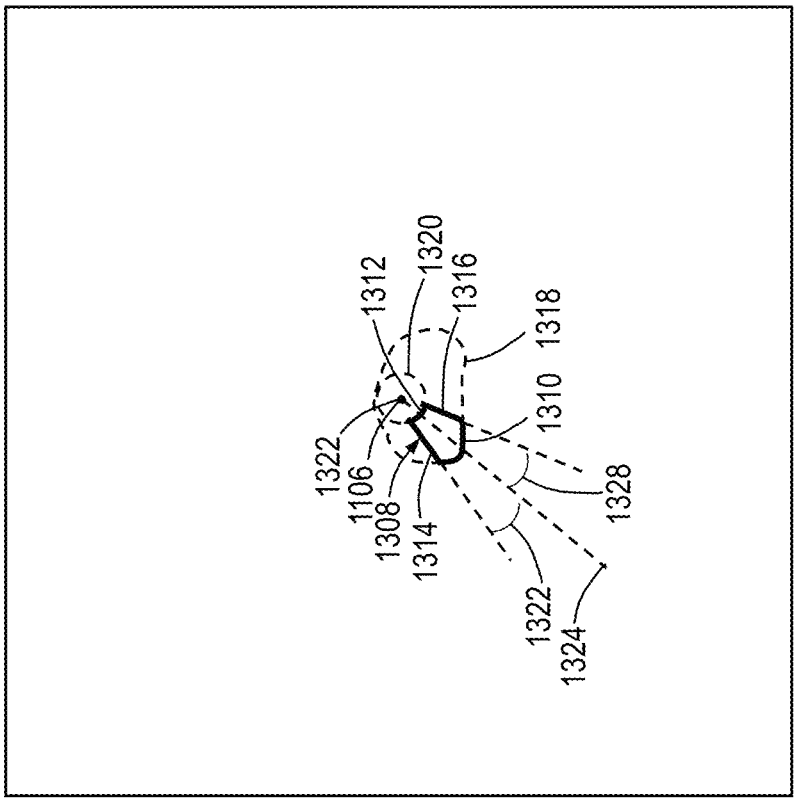
Figure 13B:
Figure 13C:
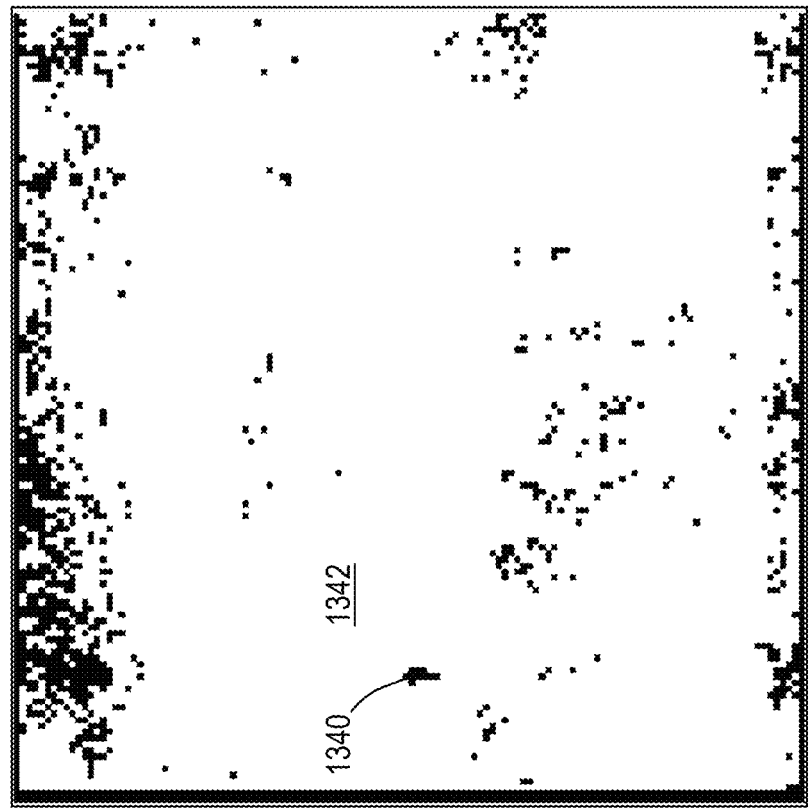

FIG. 10. is a table that identifies three different types of structural masks, in accordance with some embodiments;

FIGS. 11A-11C are representations of masks shown in FIG. 10, in accordance with at least some embodiments;

FIG. 12. is a table that identifies three different types of dynamic masks, in accordance with at least some embodiments;

FIGS. 13A-13C are enlarged representations of masks shown in FIG. 12, in accordance with at least some embodiments;

FIG. 14. is a table that shows five different types of dynamic corrections that may be employed, in accordance with at least some embodiments.

Figure 15:
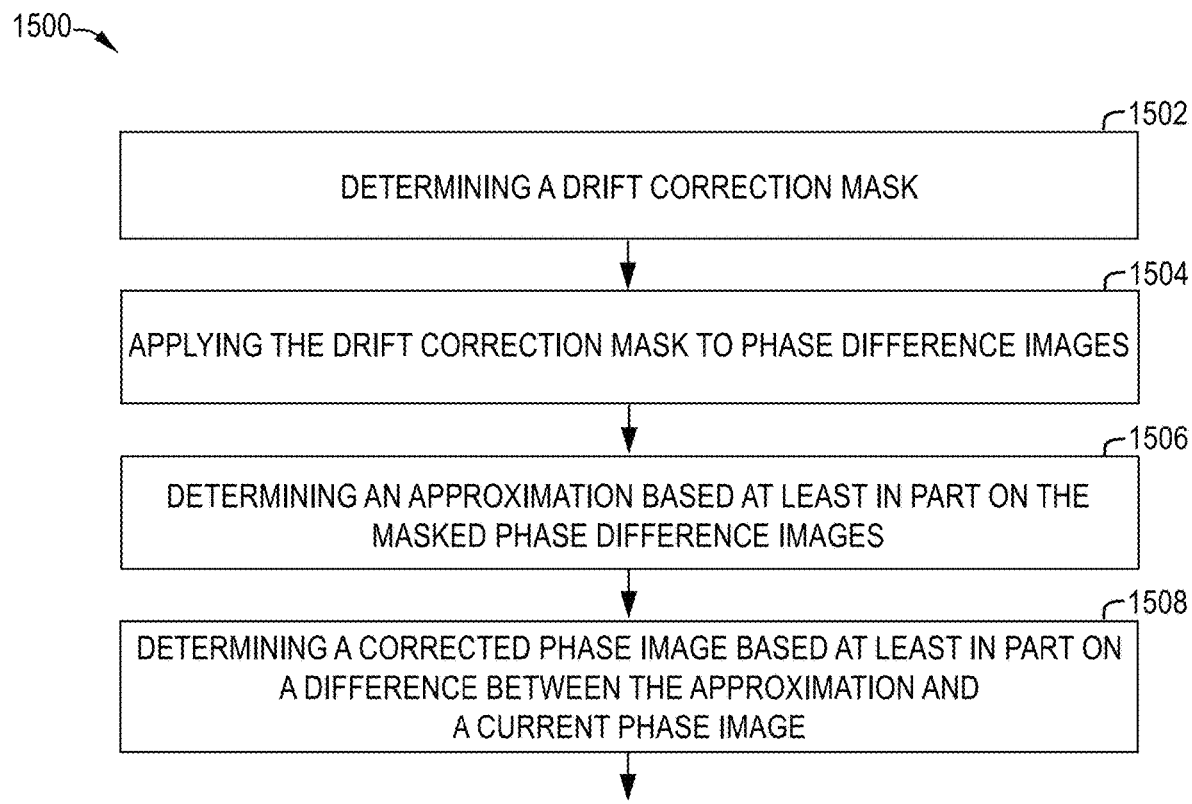
Figures 16A, 16B:
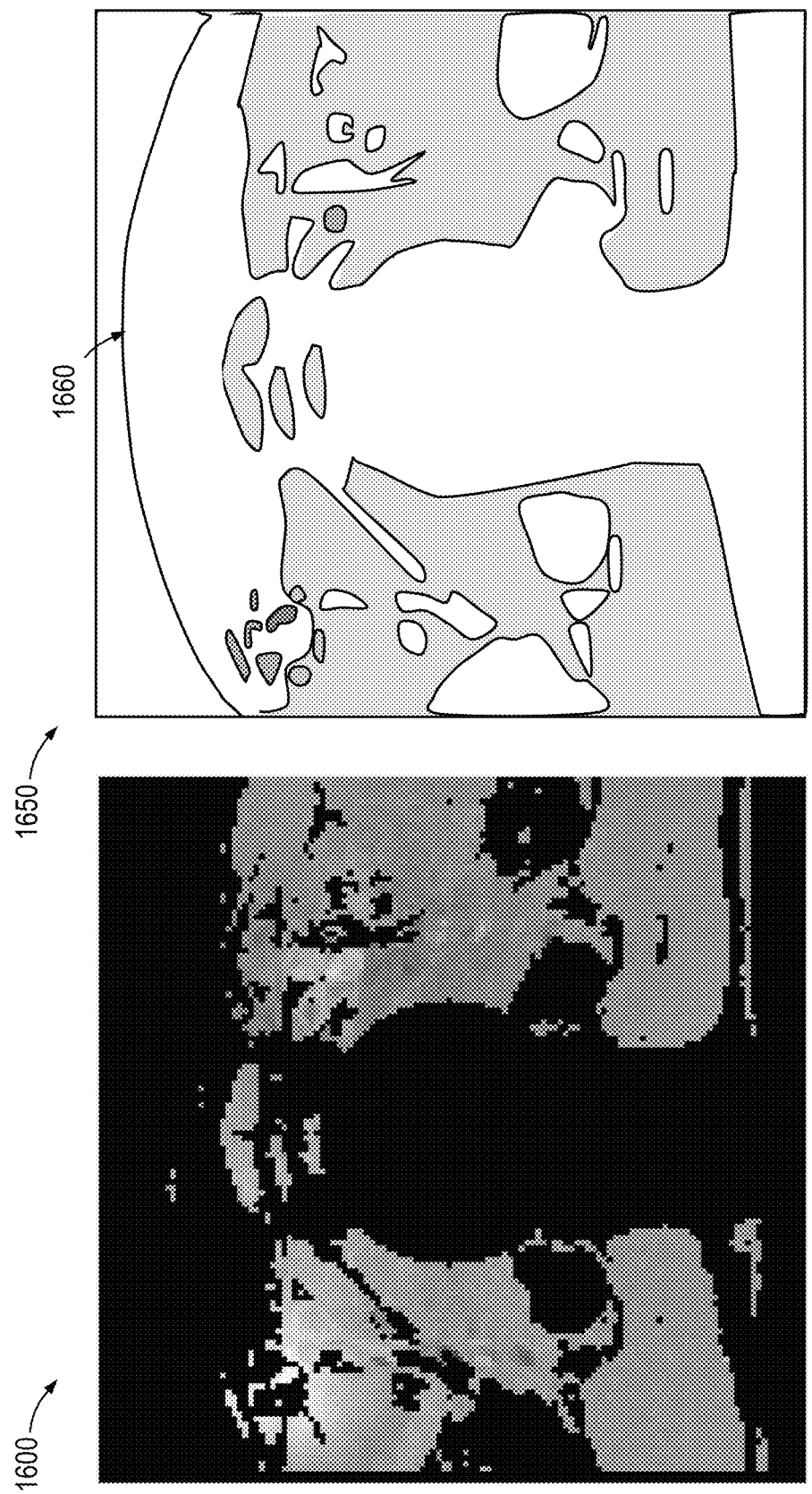
Figure 17:
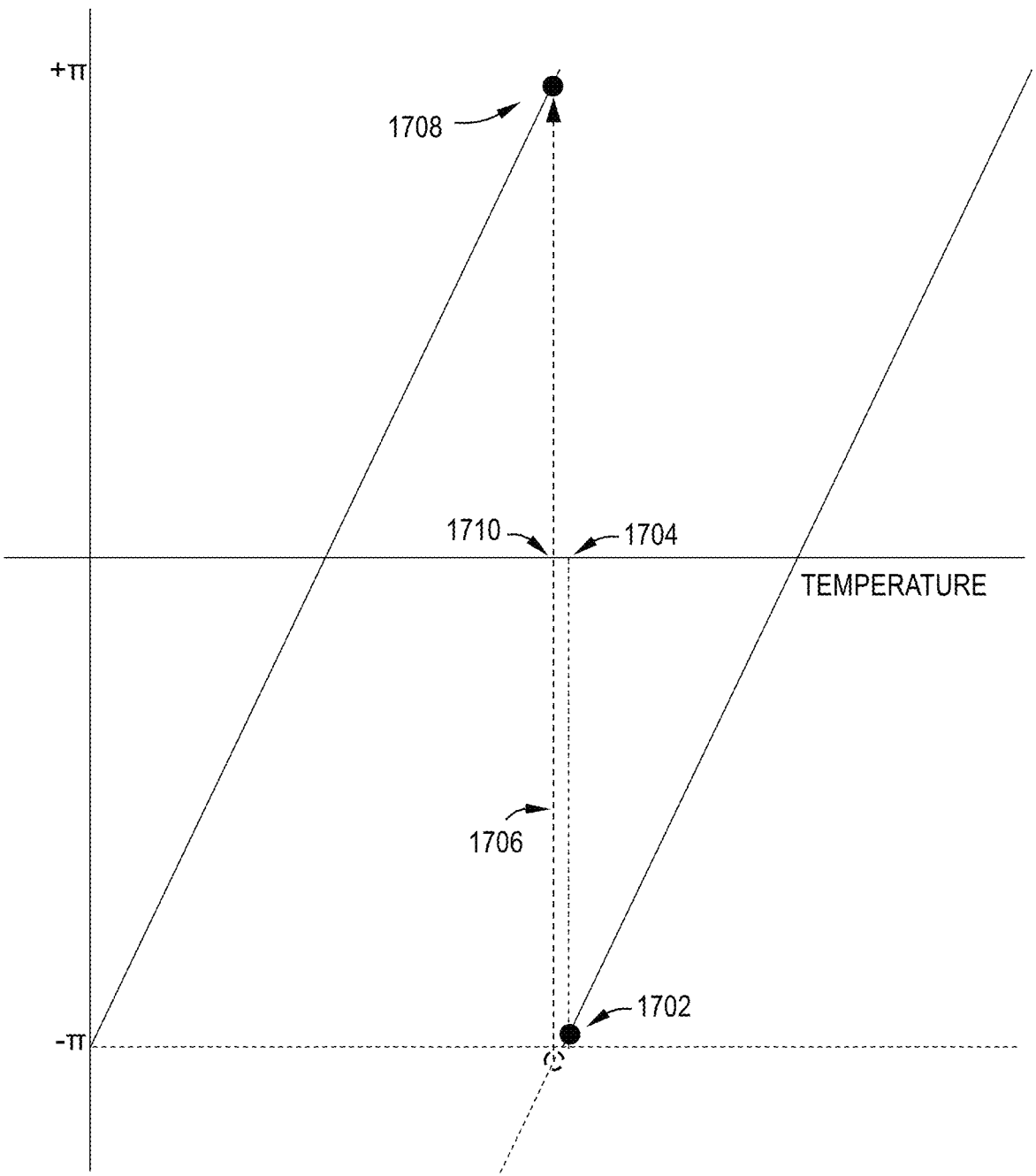
Figure 18:
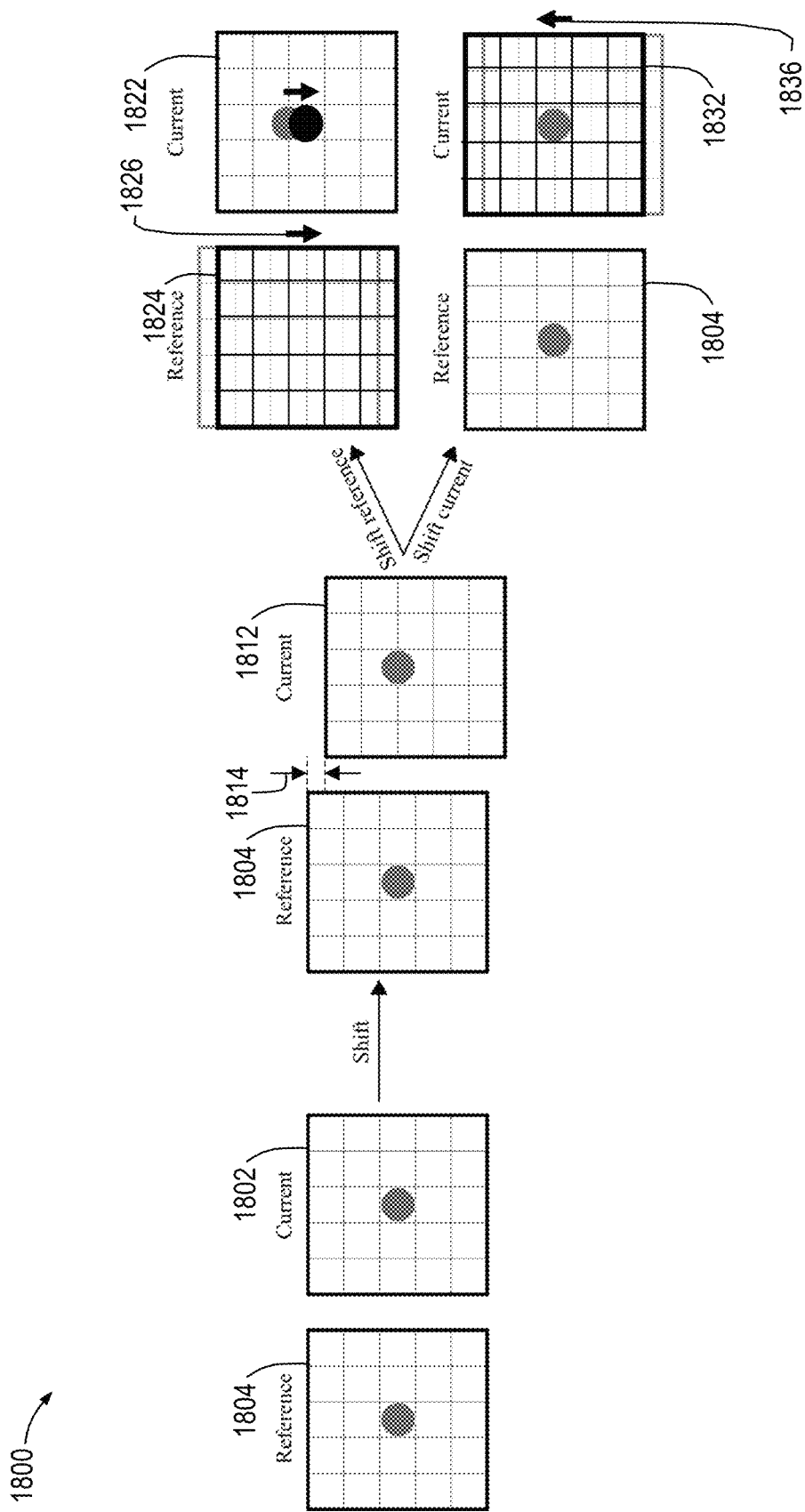
Figure 19:
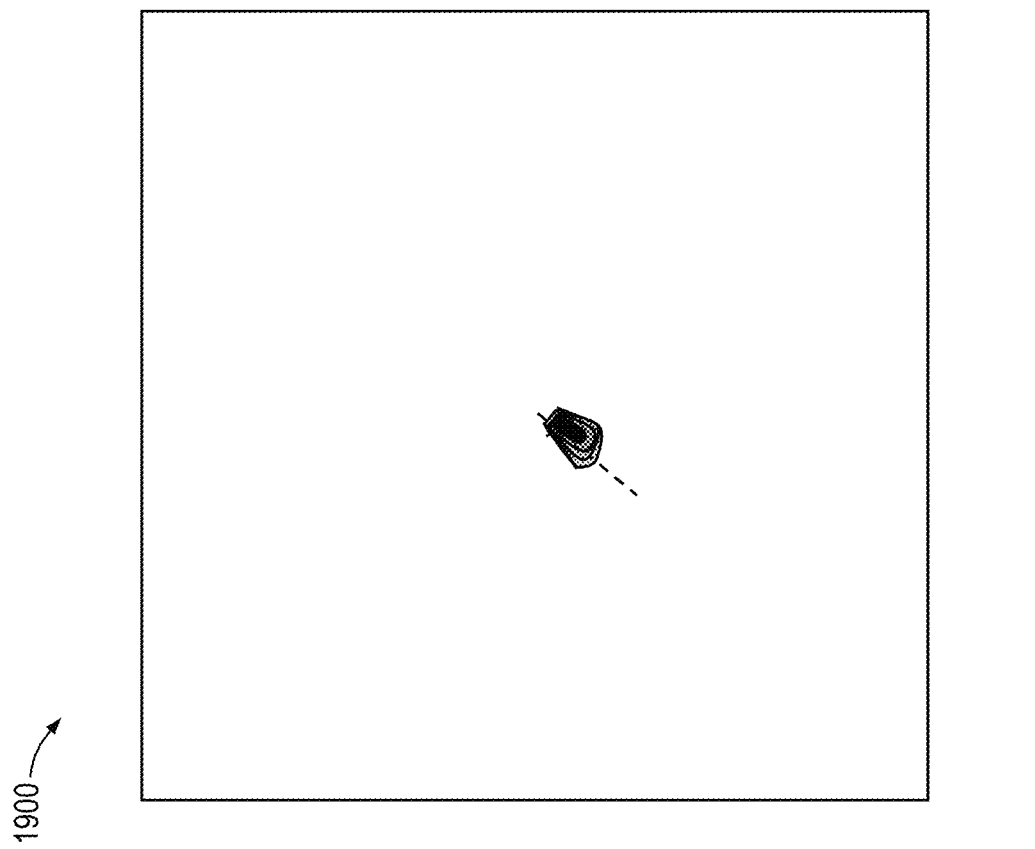

FIG. 15 is a flowchart of a method, in accordance with at least some embodiments;

FIG. 16A is a visualization of an image, in accordance with at least some embodiments;

FIG. 16B is a visualization of an image, in accordance with at least some embodiments;

FIG. 17 is a graphical representation of one type of phase wrap, in accordance with at least some embodiments;

FIG. 18 are representations of a current image and a corresponding reference image, in accordance with at least some embodiments;

FIG. 19 is a visualization of an image, in accordance with at least some embodiments.

Figure 20:
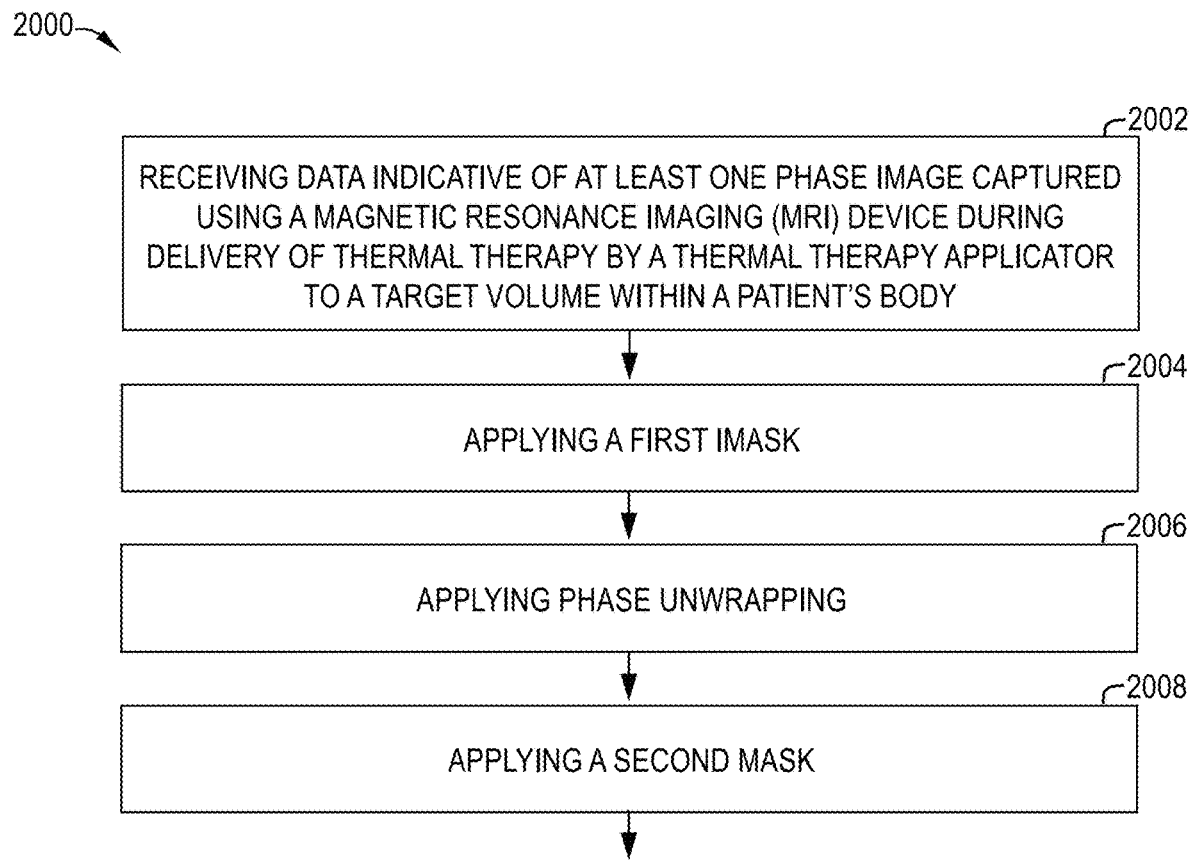
Figure 21A:
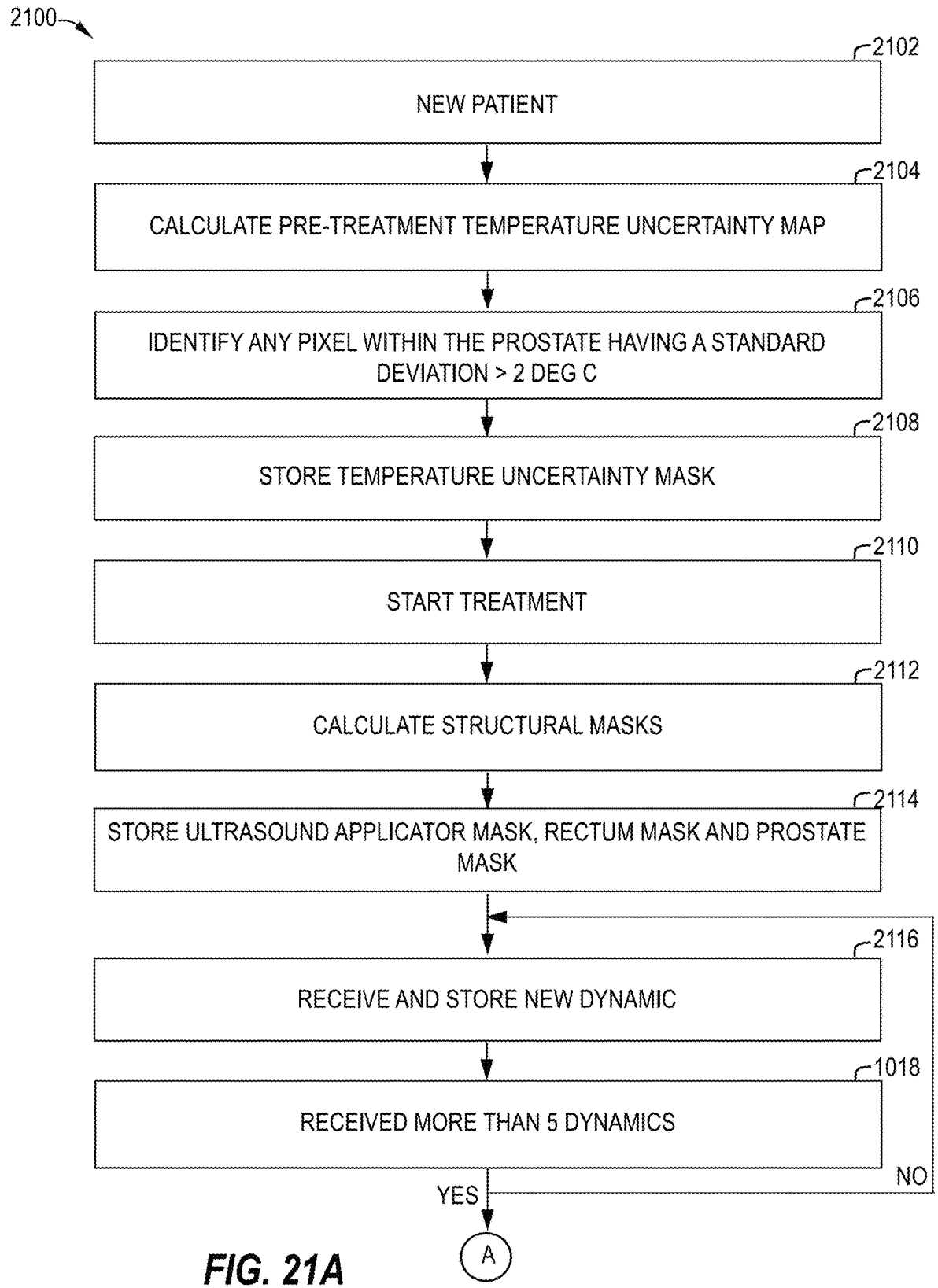
Figure 21B:
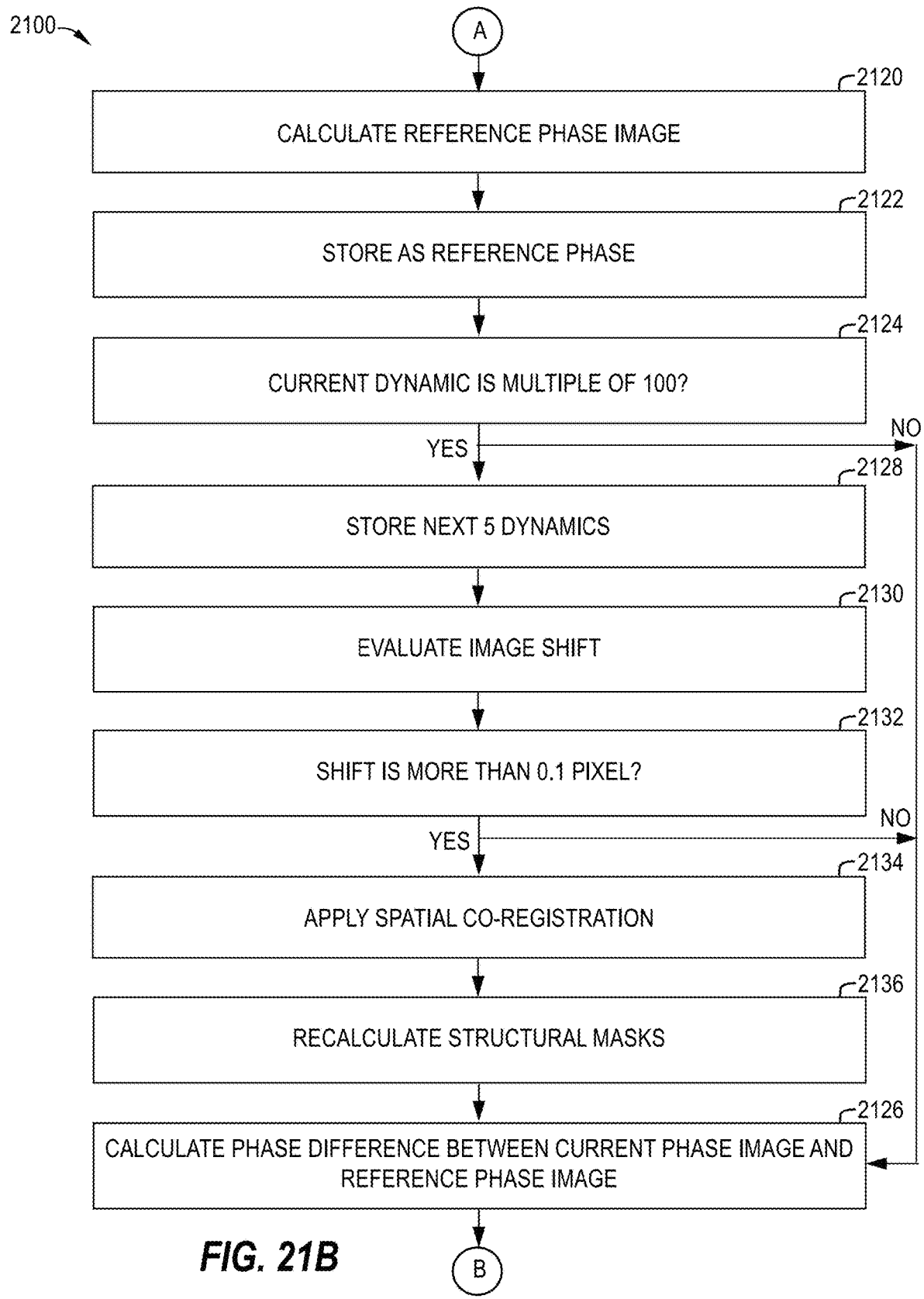
Figure 21C:
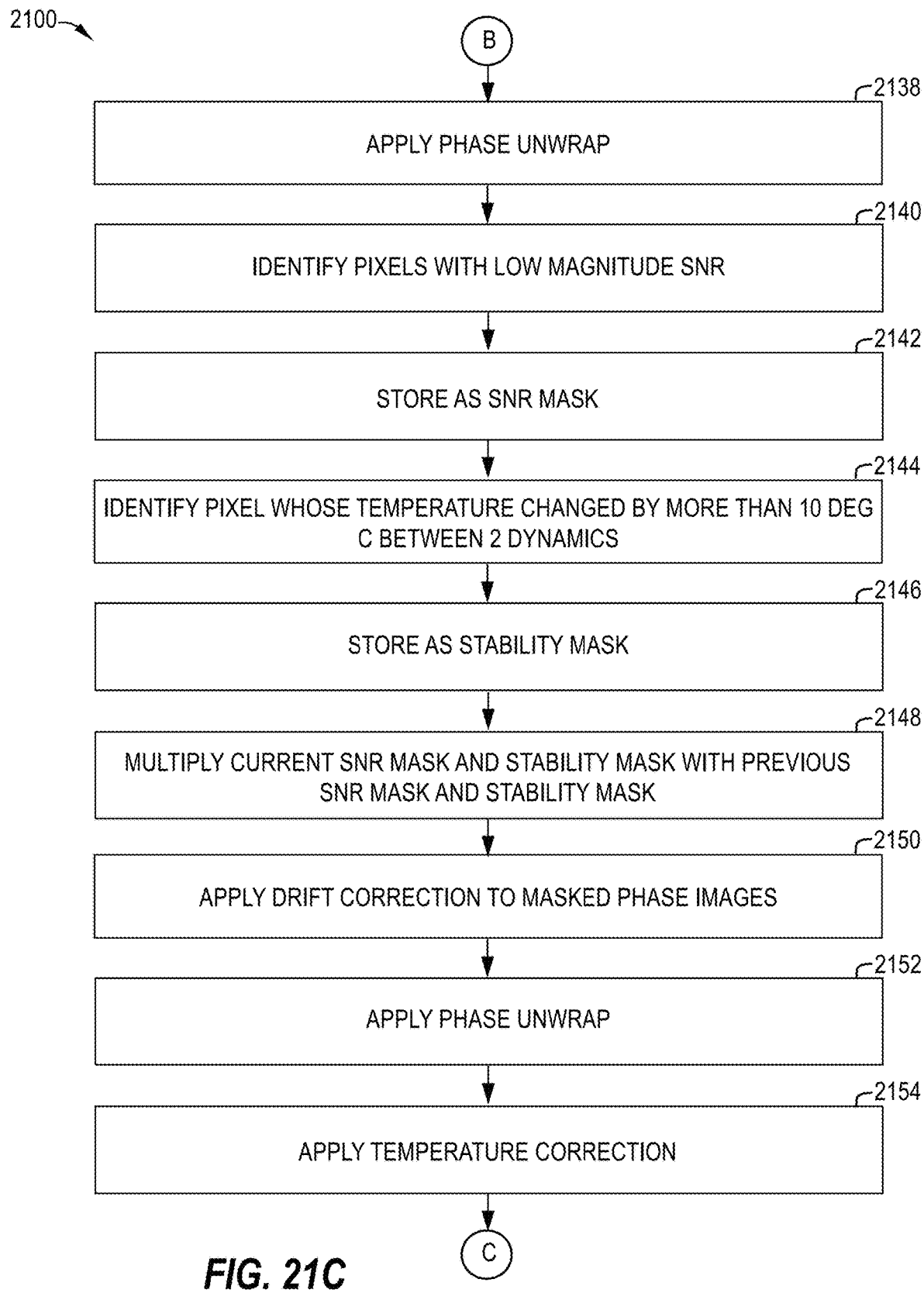
Figure 21D:
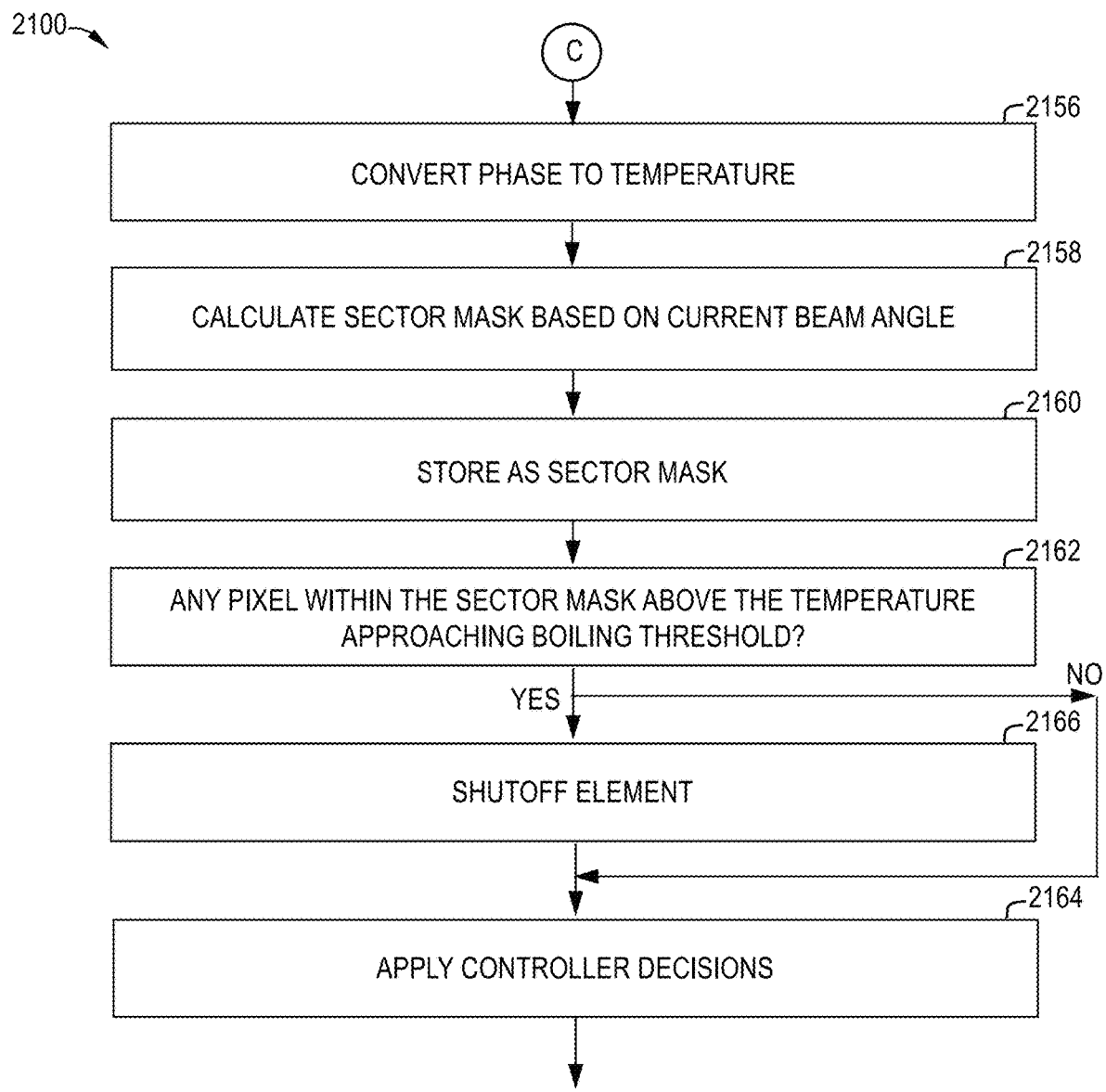
Figure 22:
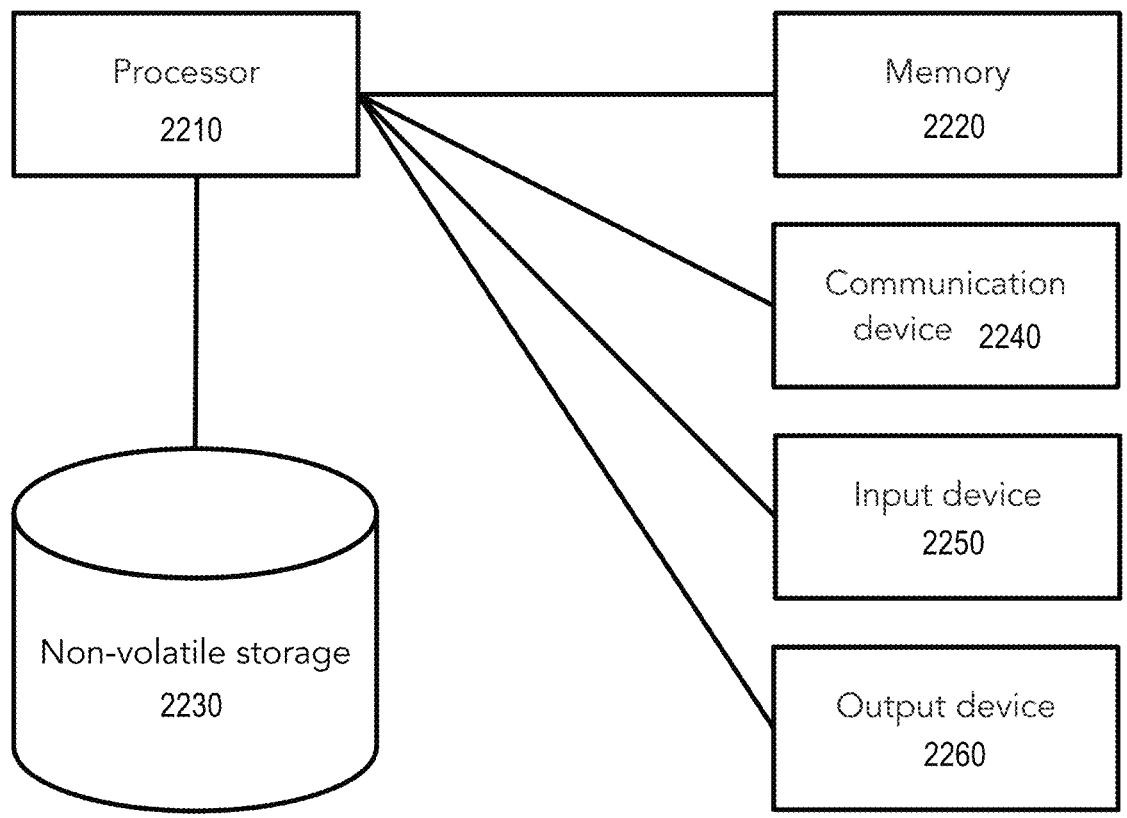

FIG. 20 is a flowchart of a method, in accordance with at least some embodiments;

FIG. 21A-D illustrate flowcharts of a method, in accordance with at least some embodiments; and FIG. 22 is a block diagram of an architecture, in accordance with at least some embodiments.

DETAILED DESCRIPTION

As stated above, it has been determined that it is possible to further reduce the effects of errors and/or potential errors in systems and methods that use temperature measurements derived from magnetic resonance imaging (MRI).

At least some aspects disclosed herein have the ability to address noise from various sources, including: magnetic resonance (MR) artifacts, frequency drift, low SNR regions, non-uniform tissue structures and/or others.

Accordingly, improved accuracy and/or efficiency of delivery of MRI-guided thermal therapies and/or other systems and methods is made possible.

At least some aspects disclosed herein employ one or more dynamic correction methodologies during thermal treatment or other procedure, since noise levels can change over time.

Various aspects and embodiments thereof will be discussed below after a brief description of one type of system in which at least some of the dynamic correction methods disclosed herein are employed.

Figure 1:
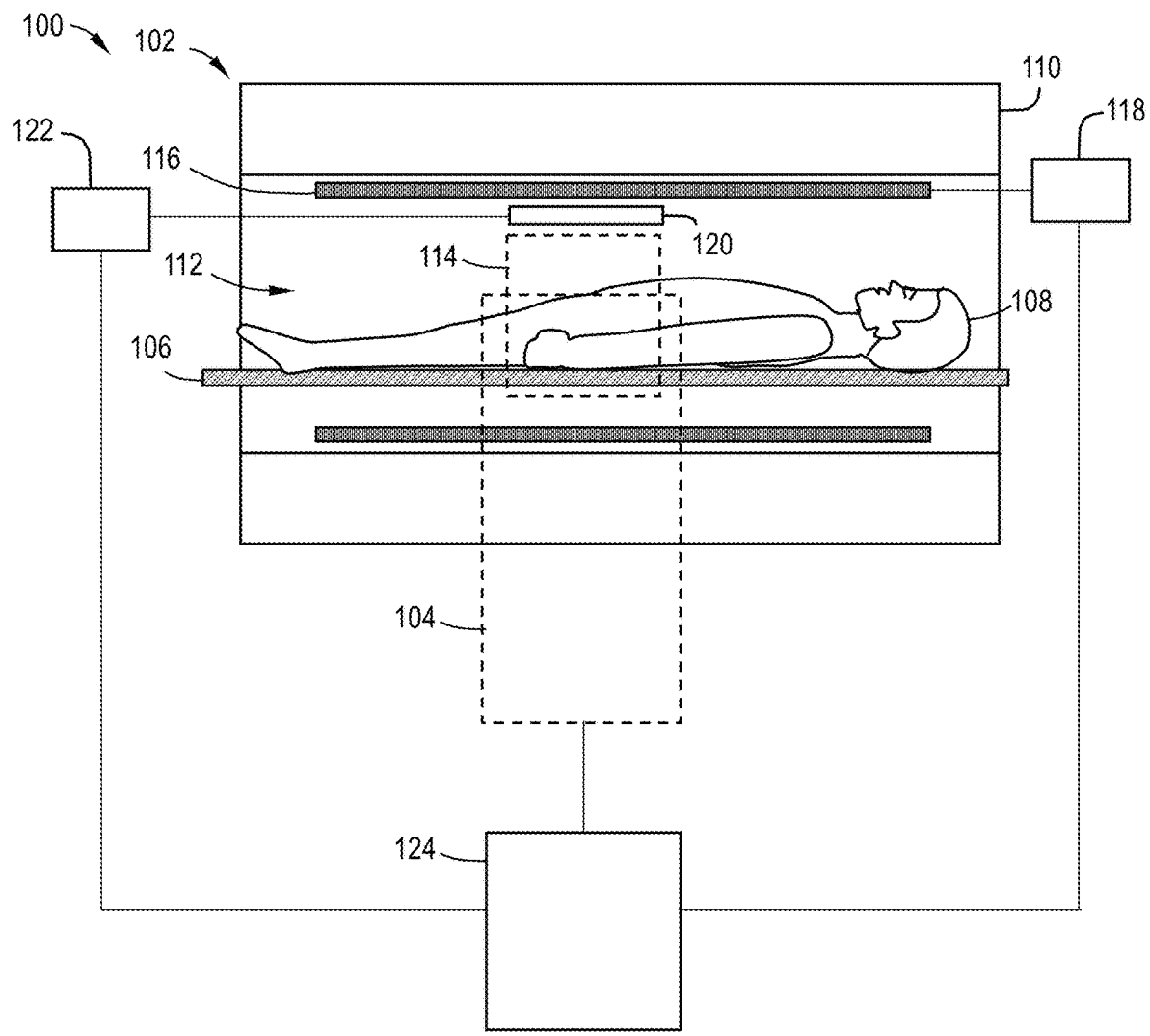
FIG. 1 is a diagram of one type of system in which at least some of the methods disclosed herein are employed, in accordance with at least some embodiments.

FIG. 1 is one type of system 100 in which at least some of the dynamic correction methods disclosed herein are employed, in accordance with at least some embodiments.

Referring to FIG. 1, the system 100, which is a medical system, includes a patient support 106 (on which a patient 108 is shown), a magnetic resonance system 102 and an image guided thermal therapy system 104.

The magnetic resonance system 102 includes a magnet 110 disposed about an opening 112, an imaging zone 114 in which the magnetic field is strong and uniform enough to perform magnetic resonance imaging, a set of magnetic field gradient coils 116 to acquire magnetic resonance data 114, a magnetic field gradient coil power supply 118 that supplies current to the magnetic field gradient coils 116 and is controlled as a function of time, a radio-frequency coil 120 to manipulate the orientations of magnetic spins within the imaging zone 114, a radio frequency transceiver 122 connected to the radio frequency coil 120, and a computer 124, which performs tasks (by executing instructions and/or otherwise) to facilitate operation of the MRI system 102 and is coupled to the radio frequency transceiver 122, the magnetic field gradient coil power supply 118, and the mage guided thermal therapy treatment system 104.

The image guided thermal therapy system 104, which will be further discussed below, performs image guided thermal therapy and implements one or more aspects and/or embodiments disclosed herein (or portion(s)) thereof to reduce the effects of errors and/or potential errors (including: magnetic resonance (MR) artifacts, frequency drift, low SNR regions, non-uniform tissue structures and/or others) and/or otherwise.

In at least some embodiments, the computer 124 of the MRI system 102 and/or one or more other computing devices (not shown) in and/or coupled to the system 100 may also perform one or more tasks (by executing instructions and/or otherwise) to implement one or more aspects and/or embodiments disclosed herein (or portion(s)) thereof to reduce the effects of errors and/or potential errors (including: magnetic resonance (MR) artifacts, frequency drift, low SNR regions, non-uniform tissue structures and/or others) and/or otherwise.

Figure 2A:
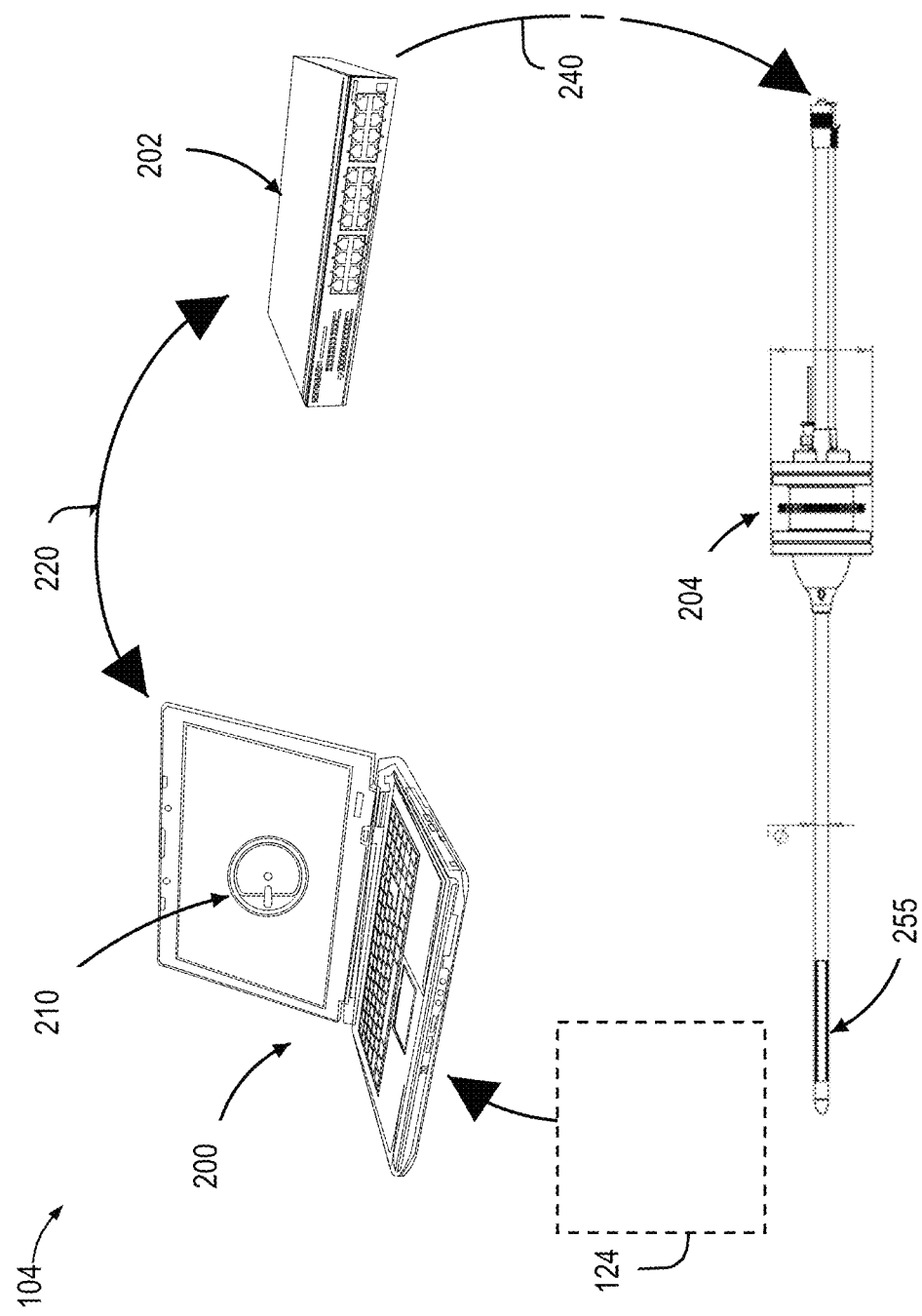
FIG. 2A is a diagram of an image-guided thermal therapy system, which may be used in the medical system of FIG. 1, in accordance with at least some embodiments.

FIG. 2A is a stylized diagram of an implementation of the image guided thermal therapy system 104, in accordance with at least some embodiments.

Referring to FIG. 2A, in accordance with at least some embodiments, the image guided thermal therapy system 104 includes a system controller 200, a therapy apparatus controller 202 and a therapy apparatus 204. The system controller 200 (which may comprise a portable PC, workstation, or any other type of processing device) may performs task (by executing instructions and/or otherwise) to facilitate operation of the image guided thermal therapy system 104 and to implement one or more aspects and/or embodiments disclosed herein (or portion(s)) thereof to reduce the effects of errors and/or potential errors (including: magnetic resonance (MR) artifacts, frequency drift, low SNR regions, non-uniform tissue structures and/or others) and/or otherwise. The system controller 200 may include a display and/or user interface 210 to facilitate user control of and/or observation of the thermal therapy treatment process, and may be coupled to and supply signals to the therapy apparatus controller 202 via communication link 220. The therapy apparatus controller 202 (which may be part of the system controller 200) may comprise analog and/or digital circuitry to determine and/or provide drive signals to be supplied to the therapy apparatus 204, and may be coupled to the therapy apparatus via a power or other communication link 240. The therapy apparatus 204 (which may be maneuvered by a motor assembly coupled thereto), may comprise an ultrasound or other treatment apparatus configured to deliver a suitable dose of ultrasound or other energy to tissue in a diseased region of a patient's body. In the illustrated embodiment, the therapy apparatus 204 comprises an elongated transurethral prostate therapy applicator having a portion 255 to be inserted longitudinally into a patient's prostate to deliver ultrasound energy to a diseased region of the patient's prostate.

The computer 124 of the MR system 102 (FIG. 1) may provide real-time (or other) images of relevant parts of the patient to the system controller 200 and/or the display and/or graphical user interface 210. The system controller 200 may use the images to monitor (in real time or otherwise) the progress or other status of the thermal therapy and may generate signals based at least in part thereon to control the therapy apparatus controller 202. Information indicative of the progress or other status may also be provided to a clinical or other operator, who may provide input (to the system controller 200 and/or the therapy apparatus controller 202) to adjust or otherwise control the thermal therapy.

The system 104 may have various operating modes.

Figure 2B:
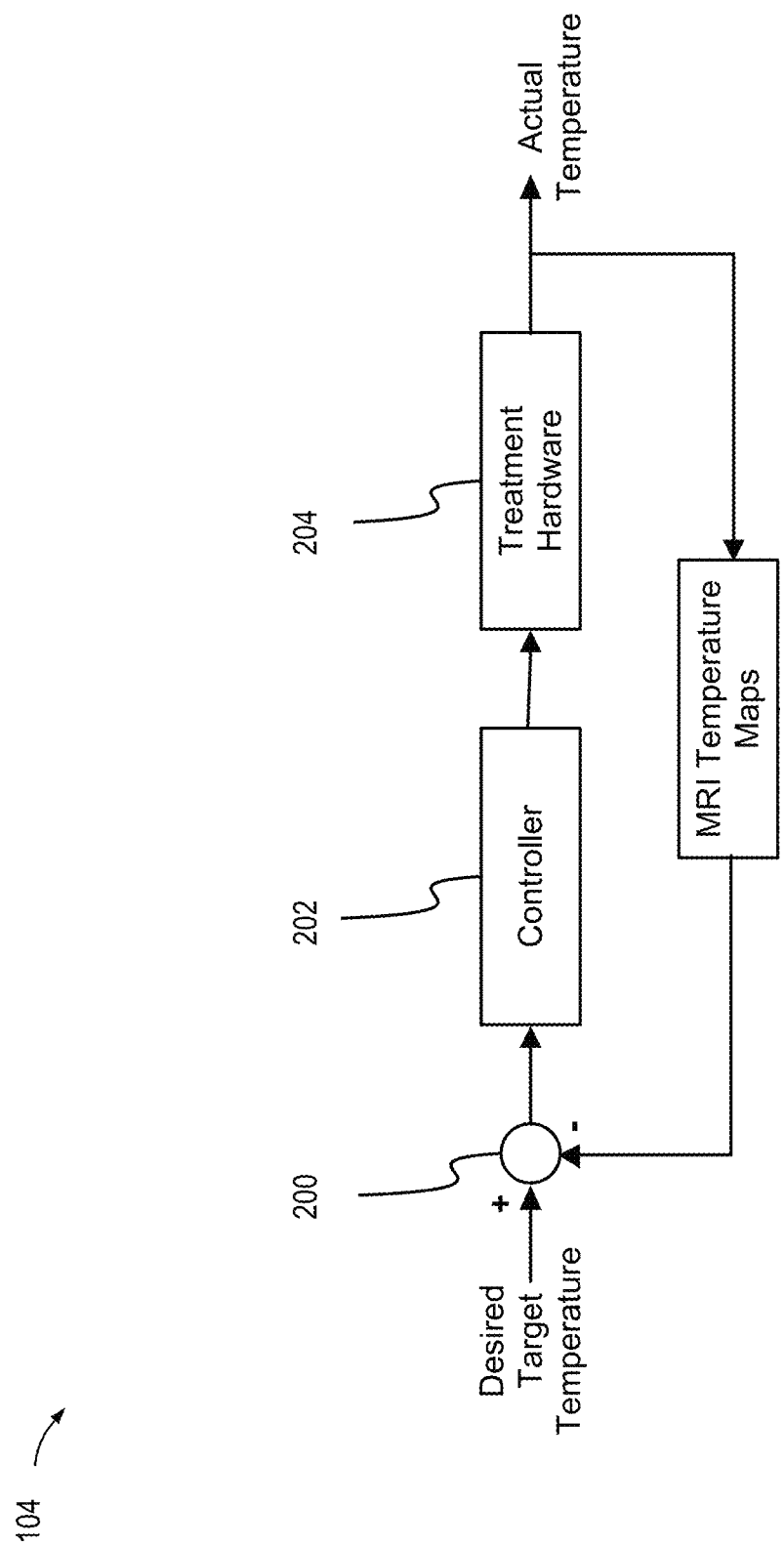
FIG. 2B is a schematic diagram of a portion of the image-guided thermal therapy system in one possible operating mode, in accordance with at least some embodiments.

FIG. 2B is a schematic diagram of a portion of the system 104 in one possible operating mode, in accordance with at least some embodiments.

Referring to FIG. 2B, the portion of the system includes an error amplifier (which may be in the system controller 200) that receives a signal indicative of a desired target temperature and further receives MRI temperature data (that is, temperature maps or other temperature data generated based at least in part on MRI data). An output from the error amplifier is supplied to the therapy apparatus controller 202, which generates drive signals that are based at least in part thereon and supplied to the therapy apparatus 204. The therapy apparatus 204 outputs ultrasonic (or other) energy based at least in part thereon to one or more regions of a patient undergoing thermal treatment. The energy raises temperatures within the region(s), which are imaged using MRI techniques. The MRI imaging is mapped to MRI temperature data, which is fed back to the error amplifier, which may adjust the output to the therapy apparatus controller 202 based at least in part thereon and/or as appropriate in subsequent steps of the treatment. This general method may be followed until treatment's goals are satisfied (e.g., a given temperature is reached in the treatment region) or an alarm or other action interrupts the process.

Figure 3:
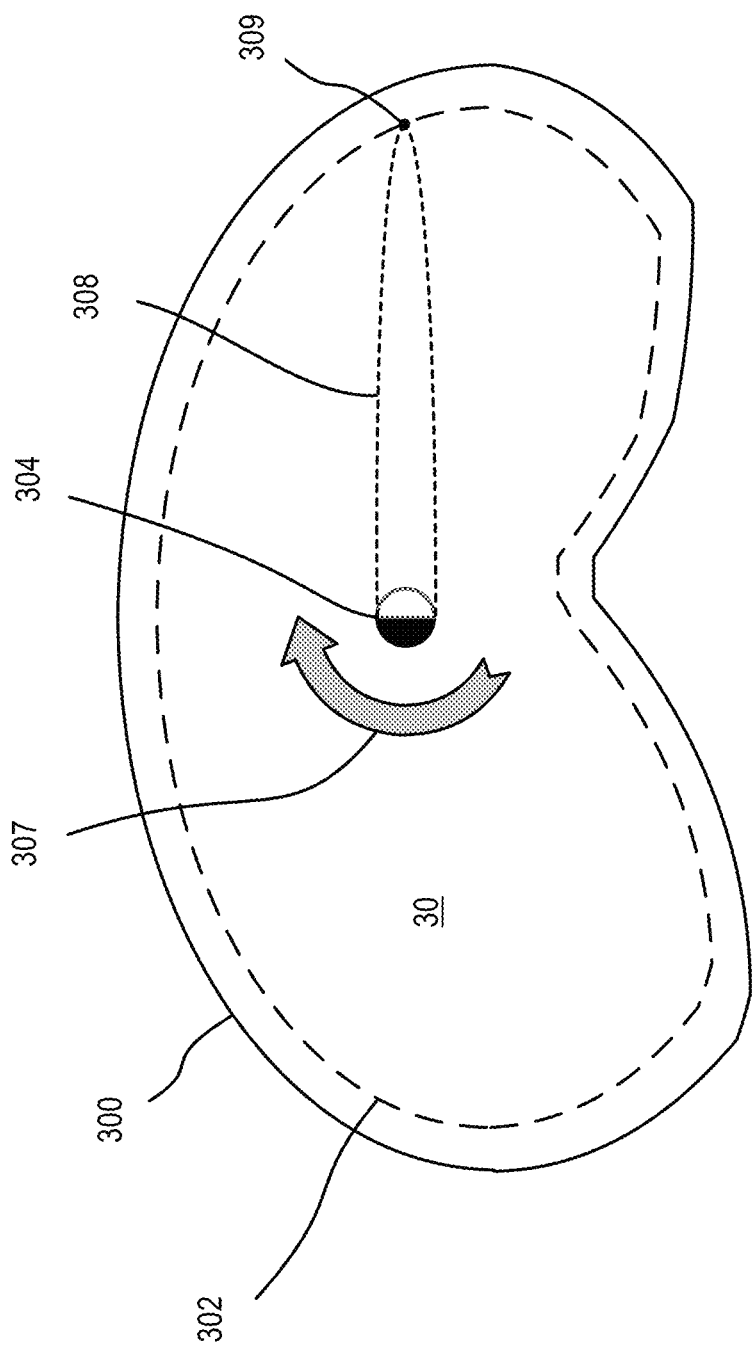
FIG. 3 illustrates a cross section of a prostate and a therapy applicator inserted therein to allow thermal therapy, in accordance with at least some embodiments.

FIG. 3 illustrates a cross section of a prostate 30 and an elongated transurethral prostate therapy applicator 304 inserted longitudinally therein to allow performance of conformal thermal therapy 308 to the prostate 30 (or a portion thereof), shown at a time t0, in accordance with at least some embodiments.

Referring to FIG. 3, in accordance with at least some embodiments, the prostate 30 has an organ boundary 300. To avoid unwanted heating outside the prostate, a treatment boundary 302 (representing a desired treatment volume), may be defined, for example, in a treatment planning step prior to or during application of the thermal therapy treatment.

As represented in the figure, and according to certain designs of applicator 304, the thermal therapy 308 may be directionally emitted from an active face of applicator 304. In view at least thereof, the location/direction of the thermal therapy 308 at any given point in time, and the location of the control point 309 at any given point in time, may depend on the angular position of applicator 304. The thermal therapy 308 is represented in the figure by a flame-shaped profile or zone (sometimes referred to herein as a treatment zone lobe) extending from the applicator 304, however the thermal therapy 308 is not limited and may instead have any suitable configuration.

In at least some embodiments, the thermal therapy applicator 304 may be rotated about its axis using a computer-controlled motor so as to sweep through the treatment volume defined by the treatment boundary 302, as described in earlier patents and applications, including: U.S. Pat. Nos. 6,589,174; 7,771,418; U.S. Pubs. 2007/0239062; 2011/0034833; U.S. patent application Publication Ser. Nos. 12/932,914; 12/932,923; 12/932,920; and 13/065,106, which are all hereby incorporated by reference.

The rotation 307 may be performed at any rate(s), which may be predetermined (e.g., planned) and/or determined dynamically during the therapy process. In at least some embodiment, applicator 304 rotates in a clockwise direction 307 as shown, but is not limited to such.

In at least some embodiments, a treatment boundary is an intended boundary within which the energy of the thermal therapy process is substantially controlled to a set-point temperature (or thermal dose) ensuring rapid and sufficient cell death of diseased cells within the interior of the volume defined by the treatment boundary. Heat can be conducted outside the treatment boundary out to the boundary of an organ (e.g., the prostate), which can be measured and controlled to achieve appropriate thermal therapy while reasonably avoiding damage to non-diseased tissues and organs proximal to said diseased locations. Tissues and organs outside the treatment boundary, even if heated, should not exceed lethal thermal dose or temperature limits.

Systems and methods for monitoring and/or controlling thermal therapy using ultrasound are described in, for example, U.S. Patent Application Publication No. 2011/0270366, titled "RF Power Controller for Ultrasound Therapy System," and U.S. Pat. No. 8,998,889, titled "System and Method for Control and Monitoring of Conformal Thermal Therapy," which are hereby incorporated by reference.

Figure 4:
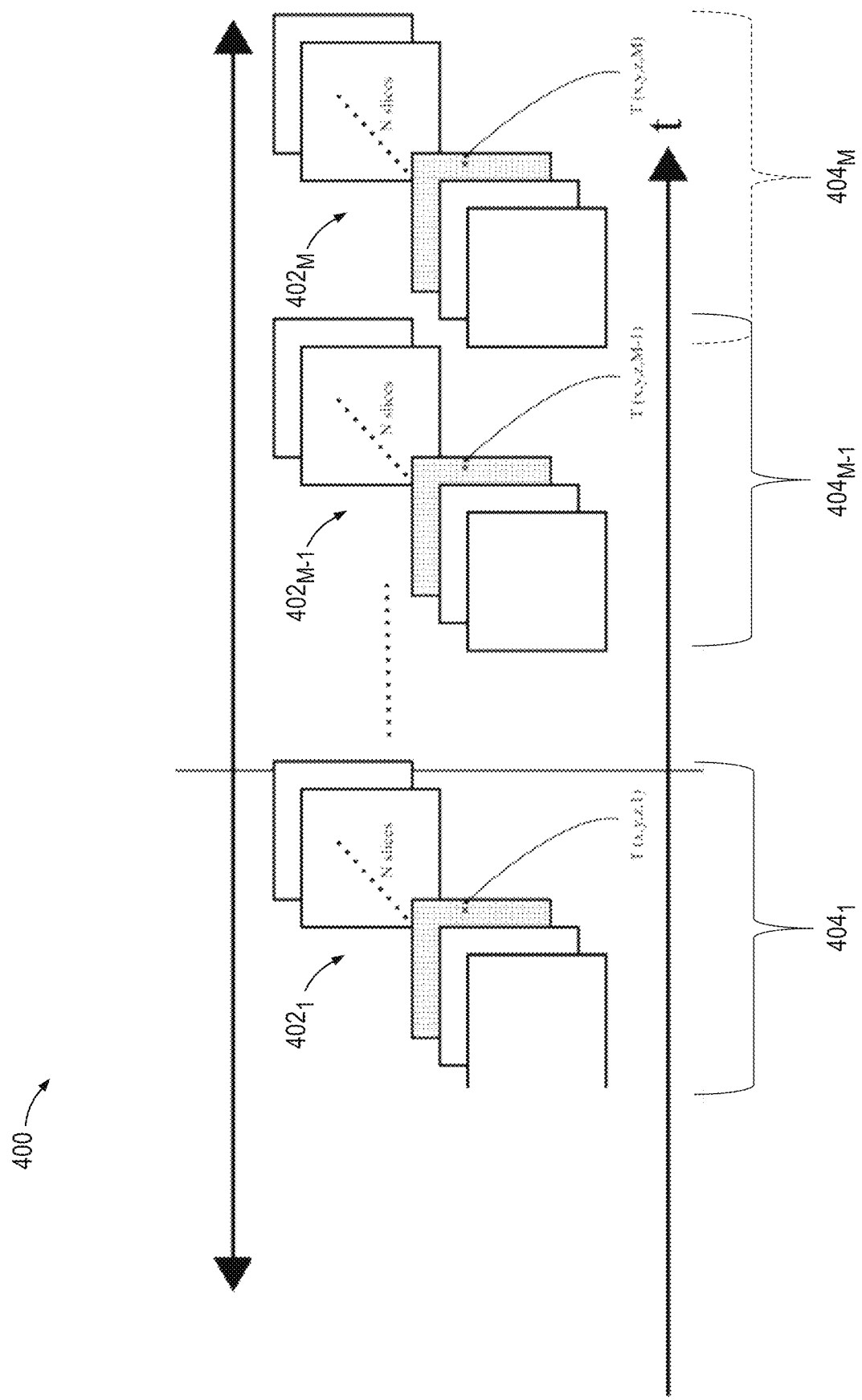
FIG. 4 is a representation of MRI image data that may be captured, in accordance with at least some embodiments.

FIG. 4 is a representation 400 of MRI image data that may be captured before, during and/or after thermal therapy, in accordance with at least some embodiments.

Referring to FIG. 4, the MRI image data may be made up of or otherwise comprise sets of MRI image data, e.g., sets of MRI image data $402_1$-$402_M$. Each set of MRI image data may include N images, e.g., cross sections (sometimes referred to as slices) and may be captured from an MRI device during a respective one of a plurality of collection periods, e.g., collection periods $404_1$-$404_M$. A collection period for a set of MRI image data is sometimes referred to herein as a dynamic.

In at least some embodiments, each set of MRI image data may comprise 12 or any other specified number of slices. The amount of time, sometimes referred to herein as a dynamic, needed to capture and/or receive the 12 or other specified number of slices in the set may average 6 seconds or other amount of time.

In at least some embodiments, one or more sets of MRI image data corresponding to one or more dynamics may be captured prior to start of therapy and used in determining a set of reference images. In at least some embodiments, the set of reference images will include one reference image for each slice in a set of MRI image data. In at least some embodiments, each reference image (phase or otherwise) may be generated by taking the mean of five or other number of images (phase or otherwise).

Unless stated otherwise, an "image" is a representation (exact or otherwise (i.e., non-exact)) of one or more objects (e.g., a body (or portion(s) thereof) of a patient, data, or any other type of object(s)) and/or one or more characteristics thereof (e.g., temperature(s) and/or other physical characteristic(s)). An image may have any form(s). For example, some images may have the form of data that may be machine readable but need not be visible to a human eye.

An image may be received from any source(s). An "MRI image" is an image that is based at least in part on MRI data. A "phase image" is an image that is based at least in part on phase data. A "magnitude image" is an image based at least in part on magnitude data. The terms "phase image" and "magnitude image" are not mutually exclusive. Thus, in at least some embodiments, an image may be both a "phase image" and a "magnitude image.

In at least some embodiments, after the start of therapy, an uncorrected temperature may be calculated or otherwise determined for each pixel (in any given measurement image) as a difference between a phase of the pixel in the measurement image and a phase of the pixel in the corresponding reference image, multiplied by a constant. The phase differences that are determined for the plurality of pixels in any given measurement image are sometimes collectively referred to herein as a phase difference image (or a phase difference).

In at least some embodiments, phase images collected during a dynamic may be processed to form a temperature map. Each temperature map may be stored in a buffer that has a width of M temperature maps (corresponding to M dynamics) and may be used to hold a rolling window of M temperature maps that may be used to calculate a temperature uncertainty map.

In at least some embodiments, the MR image data comprises measurements (of radio frequency signals emitted by atomic spins) recorded by the antenna of a Magnetic resonance apparatus during a magnetic resonance imaging scan which contains information which may be used for MR thermometry. In at least some embodiments, MR thermometry functions by measuring changes in temperature sensitive parameters. Examples of such parameters are: the proton resonance frequency shift, the diffusion coefficient, or changes in the T1 and/or T2 relaxation time may be used to measure the temperature using magnetic resonance. One of the most useful of the above measures the proton resonance frequency (PRF) shift of water protons. The resonant frequency of the protons is temperature dependent. As temperature changes in a voxel (an element in an array of volume) the frequency shifts, which causes the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Thus, at least some embodiments may rely on the proton resonant frequency shift which is known to vary with temperature according to the formula:

$$T = \Delta^\sigma * 12 * \alpha * Bo * \gamma * TE + \text{BaseTemp}$$

where T=temperature in degrees, $\Delta^\sigma$=phase difference, $\alpha$=thermal shift coefficient (ppm/° C.), Bo=magnetic field strength (Tesla), $\gamma$=gyromagnetic ratio for H+ nuclei (MHz/Tesla), TE=echo time (sec), BaseTemp=base temperature.

Since the thermometry formula is based on the PRF-sensitivity of water content in tissues, in at least some embodiments, lipid and bone tissues produces unreliable temperature measurements which can be excluded from the thermometry region of interest when making temperature-based decisions.

Figure 5B:
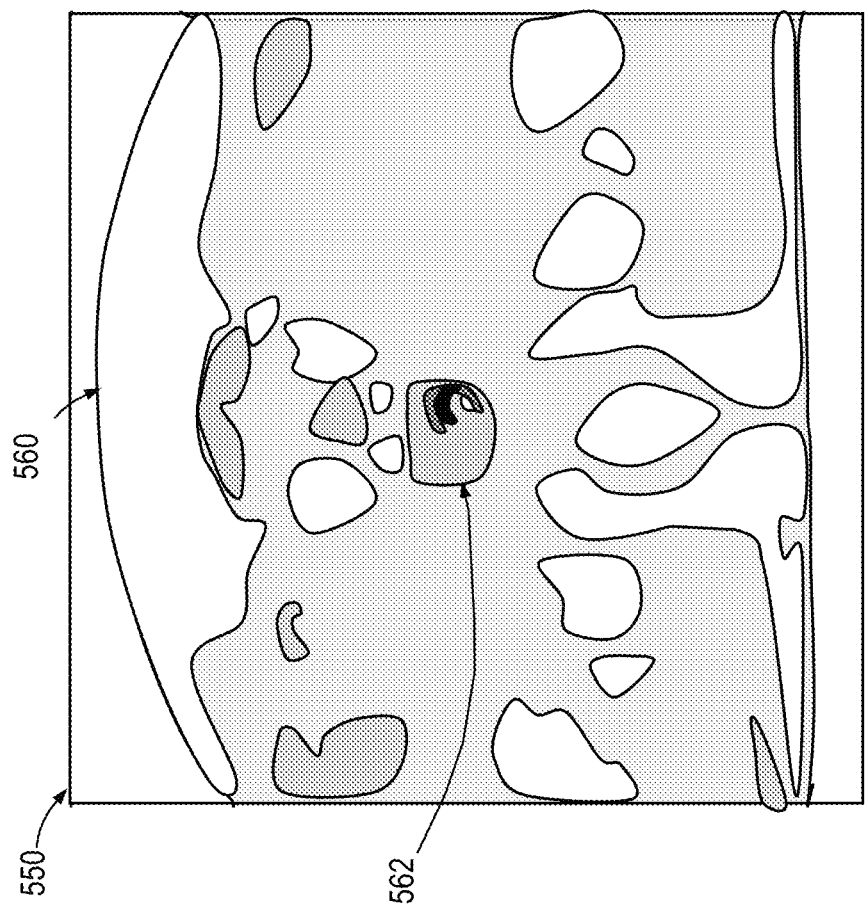
FIG. 5B is a visualization of an image, in accordance with at least some embodiments.
Figure 5A:
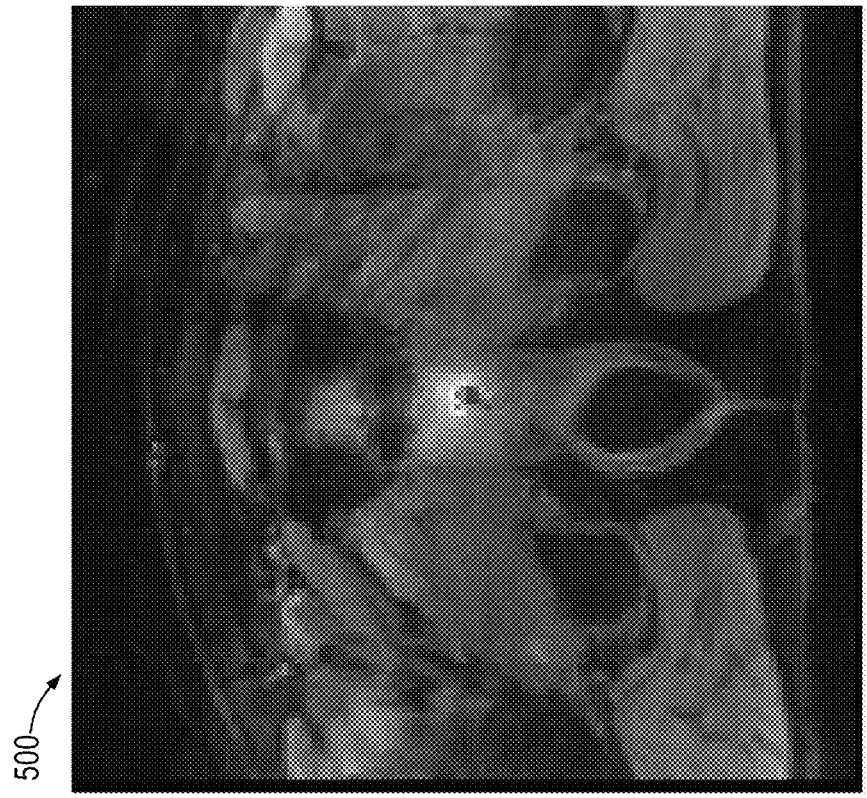
FIG. 5A is a visualization of an image, in accordance with at least some embodiments.

FIG. 5A is a visualization 500 of one of the images in one of the sets of MRI images, e.g., one image in the set of MRI images $402_1$, showing temperature information for a portion of the patient's body in the vicinity of the treatment volume at a given point in time during a thermal therapy, in accordance with at least some embodiments.

Referring to FIG. 5A, the visualization 500 employs a grayscale (i.e., different shades of gray) to indicate different temperatures. In the illustrated embodiment, the lowest temperatures are shown in black. Increasingly higher temperatures are shown in increasingly lighter shades. The highest temperatures are shown in white.

In at least some embodiments, the visualization 500 may be displayed on a visual output device such as a computer monitor screen or other display.

FIG. 5B is a visualization 550 that is similar to the visualization 500 except that: (i) the temperature information in the visualization 550 has had thresholding applied thereto (as a result, each shade in the visualization 550 corresponds to a wider temperature range than does each shade in the visualization 500) and pixels have been inverted (lowest temperatures are shown in white, increasingly higher temperatures are shown in increasingly darker shades, highest temperatures are shown in black) to assist in the teaching herein, reproduction and allow use of reference lines to point to aspects without a need for color, (ii) a border 560 has been added to identify the portion of the visualization 550 that represents a surface of the patient's body (e.g., the surface of the patient's abdomen) in the visualization 550, (iii) a border 562 has been added to identify the portion of the visualization 550 that represents a treatment boundary in the patient, and (iv) borders have been added around portions of the visualization 550 that are associated with a same temperature range (after thresholding).

In at least some embodiments, the visualization 550 may be displayed on a visual output device such as a computer monitor screen or other display.

As known in the art, each image may comprise an array of pixels. The array may have a plurality of rows and a plurality of columns, e.g., 128 rows and 128 columns, sometimes referred to herein as a 128×128 array configuration. Each pixel may define or be defined by, at least in part, a pixel value.

As used herein, a "pixel" is an element in a picture or any other type of image, of any kind, and which may or may not be visible to the human eye.

Figure 6:
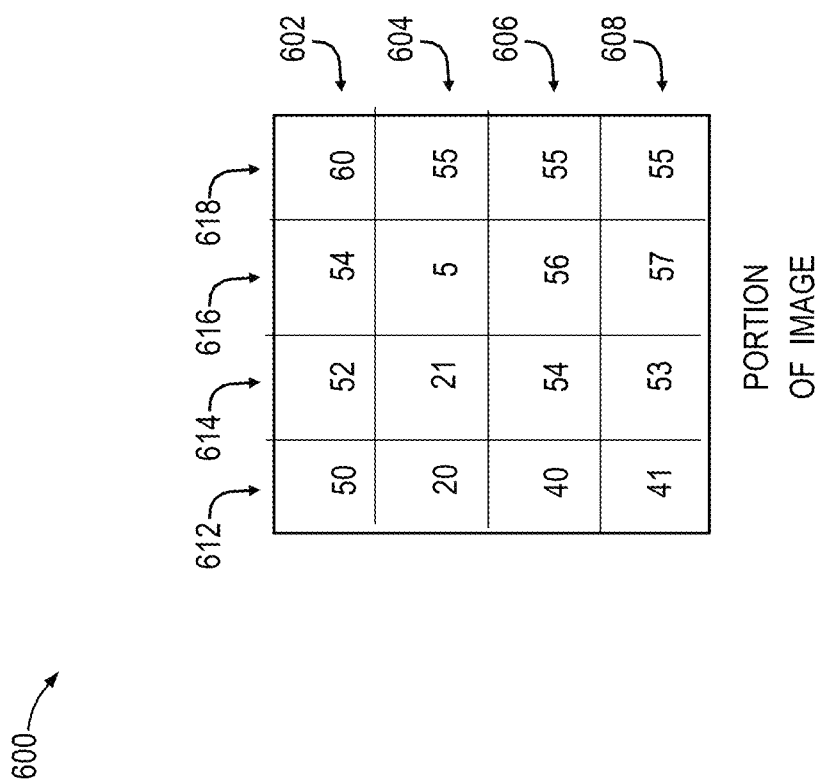
FIG. 6 is a representation of pixel values defining a portion of a pixel array, in accordance with some embodiments.

FIG. 6 is a representation 600 of pixel values defining a portion of a pixel array, in accordance with some embodiments.

Referring to FIG. 6, the portion of the pixel array has sixteen values arranged in four rows 602-608 and four columns 612-618. For example, the first row includes values 50, 52, 54, 60. The first column includes values 50, 20, 40, 41. And so on. Any given value is sometimes referred to herein as image value$_{i,j}$, where i and j refer to the row in which the value is located and the column in which the value is located, respectively.

As stated above, at least some aspects and embodiments disclosed herein apply a mask to an image.

In at least some embodiments, the mask may be defined, at least in part, by a plurality of mask values that define, at least in part, a mask array. A mask array may have a plurality of rows and a plurality of columns, and in at least some embodiments, the array will have a configuration that matches the configuration of an image to which the array is to be applied, e.g., 128×128.

The phrase "apply a mask to an image" means to generate a new (second) image (sometimes referred to herein as a masked image) or other result based at least in part on the (first) image and the mask.

Figure 7:
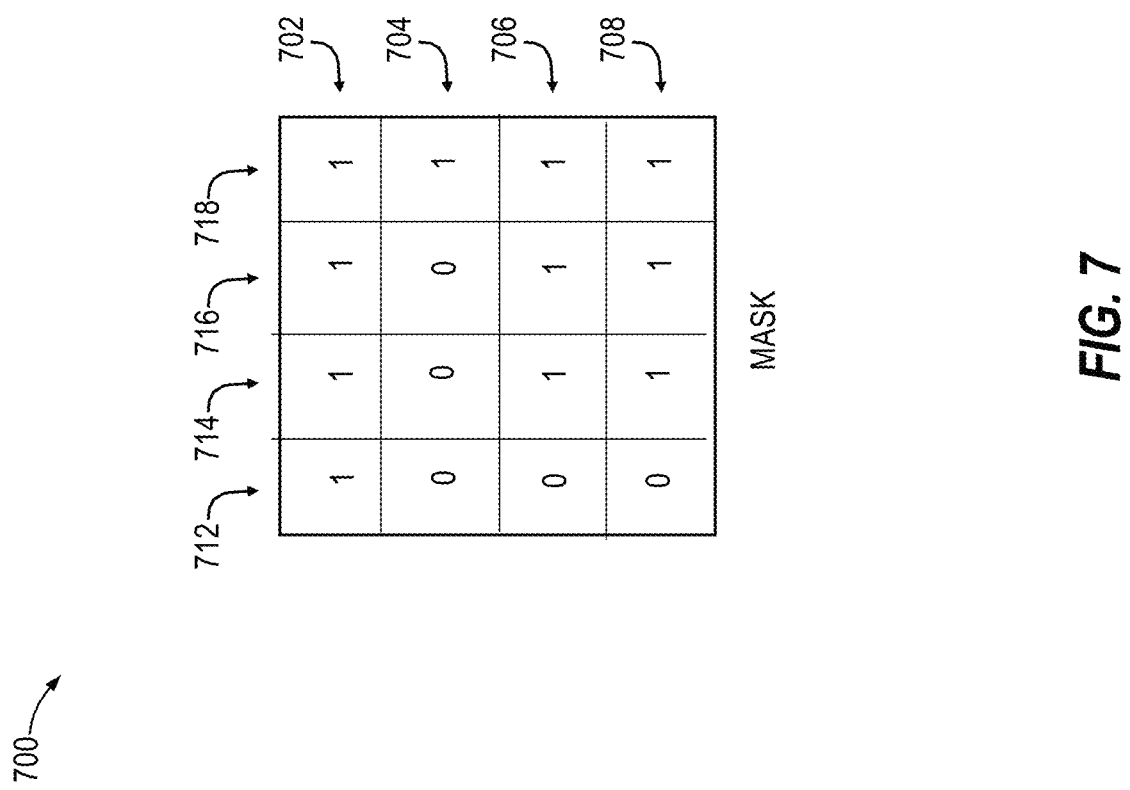
FIG. 7 is a representation of a mask, in accordance with some embodiments.

FIG. 7 is a representation 700 of a portion of a mask that may be applied to the portion of the image 600 (FIG. 6), in accordance with some embodiments.

Referring to FIG. 7, the portion of the mask array has sixteen values arranged in four rows 702-708 and four columns 712-718. For example, the first row includes values 1, 1, 1, 1. The first column includes values 1, 0, 0, 0. And so on. Any given value is sometimes referred to herein as mask value$_{i,j}$, where i and j refer to the row in which the value is associated and the column in which the value is associated, respectively.

Figure 8:
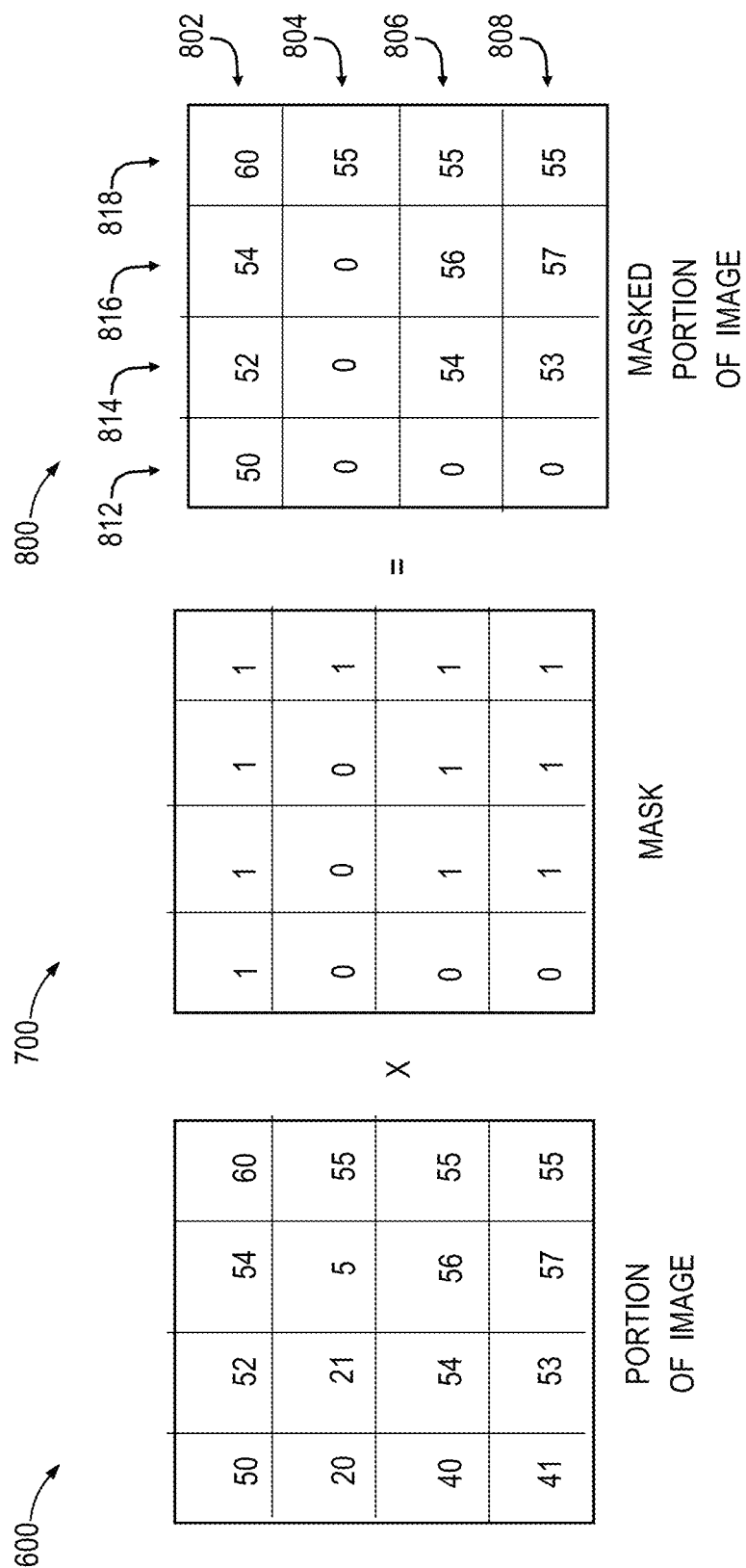
FIG. 8 is a representation of an application of a portion of a mask to a portion of an image, in accordance with some embodiments.

FIG. 8 is a representation of an application of a mask to an image, in accordance with some embodiments.

Referring to FIG. 8, in accordance with at least some embodiments, a mask, e.g., the mask 700, may be applied to an image, e.g., the image 600, to produce a masked image (sometimes referred to herein as a result or output) 800. In at least some embodiments, the masked image 800 will have a configuration that is the same (i.e., same number of rows and same number of columns) as that of the image, e.g., image 600, prior to application of the mask, e.g., mask 700. In the illustrated embodiment, for example, the masked image 801 has four rows 802-808 and four columns 812-818, which is the same configuration as that of the image 600. Any given value in the masked image is sometimes referred to herein as masked image value$_{i,j}$, where i and j refer to the row in which the value is located and the column in which the value is located, respectively.

In at least some embodiments, the application of the mask to the image comprises pixel by pixel multiplication. In other words, the value at each location in the masked image is determined as a product (multiplication) of the pixel value (for the corresponding location in the input image) and the mask value (for the corresponding location in the mask), i.e., masked image value$_{i,j}$=image value$_{i,j}$×mask value$_{i,j}$.

In the illustrated embodiment, for example, the value$_{1,1j}$ (50) in the masked image is determined as a product (multiplication) of the pixel value$_{1,1j}$ (50) in the image 600 and mask value$_{1,1j}$ (1) in the mask 700. The value$_{2,1j}$ (0) in the masked image is determined as a product (multiplication) of the pixel value$_{2,1j}$ (20) in the image 600 and mask value$_{2,1j}$ (0) in the mask 700. And so on.

Thus, in at least some embodiments, regions of the mask that have a value equal to 1 result in regions, within the masked image, where the image is the same as that of the input image (i.e., where the masked image shows the input image). Regions of the mask that have a value equal to 0 result in regions, within the masked image, where the input image is removed (i.e., where the masked image does not show the original image).

Although the mask 700 is shown with values of only 1 and 0, in at least some embodiments, masks are not limited to such, but rather may have any suitable form(s). Moreover, although the mask 700 is applied using pixel by pixel multiplication, in at least some embodiments, application of a mask is not limited to such but rather may be applied in any suitable manner(s). For example, in at least some embodiments, a mask may have values of 1 and 0.0001 (e.g., or other values that are not 0 but are small relative to the value 1), and may be applied to an image using pixel by pixel multiplication followed by thresholding to replace any masked image values below a specified threshold (e.g., a threshold near 0) with the value 0.

Pixels that are subjugated relative to other pixels are sometimes referred to herein as excluded pixels. Other pixels are sometimes referred to herein as included pixels.

In at least some embodiments, a plurality of masks may be applied to an image. In some embodiments, the masks may be applied one after the other. For example, one mask may be applied to the image and a second mask may be applied to the result thereof. In some embodiments, two or more of the masks may be combined and the combined mask may be applied to the image.

Figure 9:
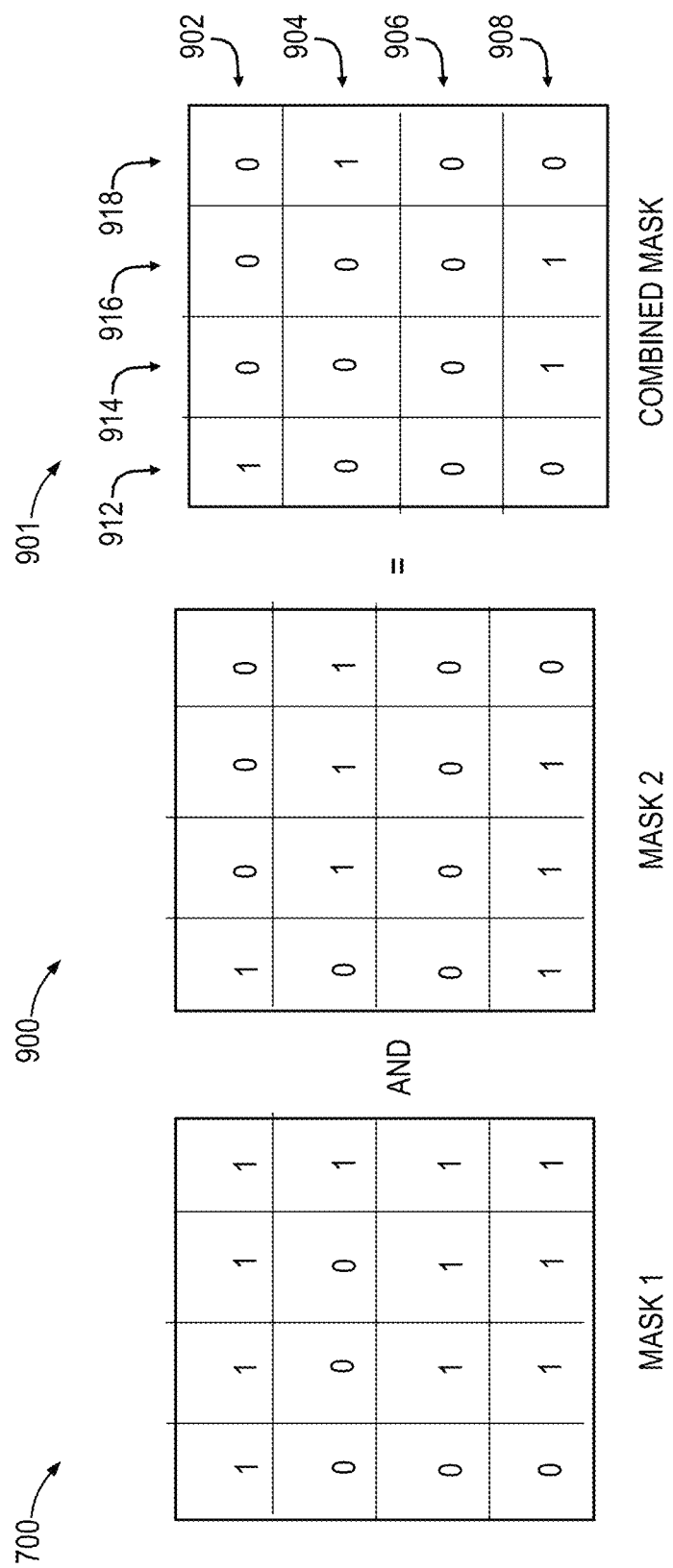
FIG. 9 is a representation of an AND operation performed on two masks; in accordance with some embodiments.

FIG. 9 is a representation of one type of BOOLEAN operation that may be used to combine masks, in accordance with some embodiments.

Referring to FIG. 9, in accordance with at least some embodiments, values of a first mask, e.g., the mask 700, may be ANDed with values of a second mask, e.g., a mask 900, to produce a combined mask 901. In at least some embodiments, the combined mask 901 will have a configuration that is the same (i.e., same number of rows and number of columns) as that of the first and second masks 700, 900, respectively. In the illustrated embodiment, for example, the combined masked 901 has four rows 902-908 and four columns 912-918, which is the same configuration as that of the first and second masks 700, 900. Any given value in the combined mask 901 is sometimes referred to herein as combined mask value$_{i,j}$, where i and j refer to the row with which the value is associated and the column with which the value is associated, respectively.

In at least some embodiments, the combining of the masks comprises value by value ANDing. In other words, the value at each location in the combined masked is determined by ANDing the mask value (for the corresponding location in the first mask) and the mask value (for the corresponding location in the second mask), i.e., combined masked value$_{i,j}$=first mask value$_{i,j}$ AND second mask value$_{i,j}$.

In the illustrated embodiment, for example, the value$_{1,1j}$ (1) in the combined mask is determined by ANDing the mask value$_{1,1j}$ (1) in the first mask 700 and mask value$_{1,1j}$ (1) in the second mask 900. The value$_{2,1j}$ (0) in the combined mask is determined by ANDing the mask value$_{2,1j}$ (0) in the first mask 700 and mask value$_{2,1j}$ (0) in the second mask 900. And so on.

The combined mask 901 includes the first mask 700 and the second mask 900.

In at least some embodiments, a combined mask may be applied to an image in a similar manner as described above with respect to the first mask 700. Thus, in at least some embodiments, regions of a combined mask that have a value equal to 1 result in regions, within a masked image, where the image is the same as that of an input image (i.e., where the masked image shows the input image). Regions of a combined mask that have a value equal to 0 result in regions, within the masked image, where the input image is removed (i.e., where the masked image does not show the original image).

In at least some embodiments, the application of the combined mask 901 is in effect application of the first mask 700 and application of the second mask 900.

Notwithstanding that a Boolean operation (AND, OR, etc.) may be used to combine two or more masks, the combining of masks is not limited to such. In at least some other embodiments, multiplication may be used to combine two or masks.

As stated above, in at least some embodiments, a mask may be a static mask or a dynamic mask. A static mask may be defined before treatment begins, based on user-defined landmarks or otherwise, and is not expected to change during treatment. A dynamic mask is computed or otherwise determined during treatment, and may change during treatment.

One type of static mask that may be employed is sometimes referred to herein as a temperature uncertainty (TU) mask that relates to a MRI thermometry method's finite ability to produce a temperature uncertainty map. A temperature uncertainty mask stores information identifying pixels that exhibit noise in excess of a noise threshold before the start of therapy. In at least some embodiments, a temperature uncertainty mask may be created by determining, for every pixel, a standard deviation of its pixel values across a given or other number of received images, and for each pixel for which the pixel values exceed a standard deviation of 2° C. or other noise threshold, setting or otherwise providing a flag or other indication in the mask to identify the pixel as a noisy pixel. In at least some embodiments, the mask value$_{i,j}$ corresponding to each noisy pixel$_{i,j}$ is set to or otherwise defined as 0, and mask values corresponding to other pixels are set to or otherwise defined as 1.

During thermal therapy, each pixel identified as noisy will have its pixel values replaced. In at least some embodiments, the pixel value may be replaced with an estimated pixel value. In at least some embodiments, the pixel value may be replaced with an estimated value determined by linear or other interpolation based at least in part on the four neighboring pixels (up, down, left, right) of the pixel.

Another type of static mask that may be employed is sometimes referred to herein as a structural mask. In at least some embodiments, static masks may be generated during treatment planning.

FIG. 10. is a table 1000 that identifies three different types of structural masks, characteristics thereof and representations of examples thereof (reduced in size compared to the size of the visualizations in FIG. 5A-5B), in accordance with at least some embodiments.

FIGS. 11A-11C are full size representations (compared to the size of the visualizations in FIG. 5A-5B) illustrating the different regions in each of the examples in FIG. 10, in accordance with at least some embodiments.

Referring to FIG. 10 and FIGS. 11A-11C, in accordance with at least some embodiments, the three different types of structural masks are: (1) an ultrasound applicator (UA) (or other therapy applicator) mask 1100, (2) a prostate (or other target region) mask 1102, and (3) a rectum (or other restricted region) mask 1104.

The ultrasound applicator (UA) (or other therapy applicator) mask 1100 excludes or otherwise subjugates pixels that are within a specified distance of the therapy applicator or portion(s) thereof. In the illustrated embodiment, the therapy applicator comprises an ultrasound therapy applicator having a center 1106 and the mask 1100 excludes or otherwise subjugates pixels in a region 1108 within 40 mm of the center 1106 of the ultrasound therapy applicator. In at least some embodiments, this mask 1100 is slice independent.

The prostate (or other target region) mask 1102 includes pixels within a contour of a prostate (or other target region) or portion(s) thereof and excludes or otherwise subjugates others. In the illustrated embodiment, the prostate (or other target region) mask 1102 includes all pixels whose center is fully included in within a contour 1110 of the prostate (or other target region) and excludes or otherwise subjugates others. In at least some embodiments, this mask 1102 is slice dependent because the contour of the prostate (or target region) may be different in each slice of a dynamic.

The rectum (or other restricted region) mask 1104 excludes or otherwise subjugates pixels within a region having a specified positional relationship to the rectum (or other restricted region) or portion(s) thereof. In the illustrated embodiment, the rectum (or other restricted region) mask 1104 excludes pixels that are within a region 1112: (1) below the therapy applicator and (2) laterally within 15 mm (i.e., +/−15 mm) of a center 1106 of the therapy applicator.

In accordance with at least some embodiments, including the illustrated embodiment, the above structural masks are based at least in part on the position of the center of the ultrasound applicator (UA) or other therapy applicator. Consequently, if the center of the ultrasound applicator (UA) or other therapy applicator is modified during the treatment (either by the user or because of image shift—discussed below), these structural masks will have to be generated again.

As stated above, a mask may also be a dynamic mask, which may be computed or otherwise determined for every dynamic (or otherwise) during treatment, and may change during treatment.

FIG. 12. is a table 1200 that identifies three different types of dynamic masks, characteristics thereof and representations of examples thereof (reduced in size compared to the size of the visualizations in FIG. 5A-5B), in accordance with at least some embodiments.

FIGS. 13A-13C are full size representations (compared to the size of the visualizations in FIG. 5A-5B) illustrating the different regions in each of the examples in FIG. 12, in accordance with at least some embodiments.

Referring to FIG. 12 and FIGS. 13A-13C, in accordance with at least some embodiments, three different types of dynamic masks are: (1) a sector (or boiling detection) mask 1300, (2) a signal to noise ratio (SNR) mask 1302, and (3) a stability mask 1304.

The sector (or boiling detection) mask 1300 includes pixels within a sector (or other region) or portion(s) thereof receiving energy from the therapy applicator at a current (or other) point in time. In the illustrated embodiment, the sector (or boiling detection) mask 1300 includes pixels within a polygon 1308 having four sides 1310, 1312, 1314, 1316. The first side 1310 is defined by a prostate (or other target region) boundary 1318. The second side 1312 is defined by a circle 1320 having a center 1322 at the center 1106 of the therapy applicator and a radius of 6 mm (or other positional relation to the therapy applicator). The third and fourth sides 1314, 1316 are defined by lines that are disposed on opposite sides of a current therapy beam centerline 1324 (e.g., a line at the center of the thermal therapy beam and extending from the therapy applicator 304 in a direction at which the center of the thermal therapy beam is emitted a current point in time) and angularly displaced therefrom by angles 1326, 1328 of +15 degrees and −15 degrees, respectively, or some other angles.

The signal to noise ratio (SNR) mask 1302 and the stability mask 1304 are sometimes referred to herein as noise masks. In at least some embodiments, these masks are used to filter out pixels that did not appear noisy (did not exceed a noise threshold or other criteria for a noisy pixel) prior to the start of the treatment but appear noisy during the treatment. In at least some embodiments, each of these masks is cumulative, meaning that if a pixel is masked at a given dynamic, it will remain masked as such throughout the treatment. Thus, in at least some embodiments, the mask used in a given dynamic will be based at least in part on the mask used in the prior dynamic.

The stability mask 1304 is used to store information identifying any pixels that are outside the target region and/or other heating volume and exhibit large temperature variations or other noise in excess of a noise threshold after treatment is started. In at least some embodiments, the stability mask 1304 for a given dynamic may be created by determining, for pixels outside the target region or other heating volume, a difference between its temperature in that dynamic and its temperature in a prior dynamic (e.g., temperature of pixel$_{i,j}$ of slice$_k$ for dynamic$_{current}$−temperature of pixel$_{i,j}$ of slice$_k$ for dynami$_{current-1}$), and for each of such pixels for which the temperature difference exceeds 10° C. (or other difference threshold) or other noise criteria, setting or otherwise providing a flag or other indication in the stability mask to identify the pixel as a noisy pixel. In at least some embodiments, the mask value$_{i,j}$ corresponding to each noisy pixel$_{i,j}$ is set to or otherwise defined as 0, and mask values corresponding to other pixels are set to or otherwise defined as 1. See for example mask values in a region 1340 corresponding to noisy pixels and set to 0, and mask values in a region 1342 corresponding to other pixels and set to 1.

In at least some embodiments, the pixels outside of the target region or other heating volume will be those pixels that are not included in or are otherwise subjugated in the prostate (or other target region) mask. Thus, in at least some embodiments, the stability mask 1304 will be based at least in part on a prostate (or other target region) mask.

As stated above, in at least some embodiments, the stability mask 1304 is cumulative, meaning that if a pixel is masked at a given dynamic, it will remain masked as such throughout the treatment. Thus, in at least some embodiments, the stability mask 1304 used in a given dynamic will be based at least in part on the stability mask 1304 used in the prior dynamic. In at least some embodiments, a stability mask 1304 for a given dynamic is made cumulative by determining the stability mask 1304 as described above and multiplying it by the stability mask 1304 used in the prior dynamic.

During therapy, each pixel identified as a noisy pixel will have its pixel values replaced and/or ignored. If it is to be replaced, it may be replaced with an estimated pixel value determined by linear or other interpolation based at least in part on the values of the four neighboring pixels (up, down, left, right) of the pixel.

Accurate temperature measurements require pixels with a high signal to noise ratio (SNR). The SNR mask 1302 identifies pixels that have a satisfactory SNR (e.g., an SNR that satisfies an SNR criteria). In at least some embodiments, the SNR mask 1302 is generated by thresholding magnitude images using Otsu's method. In at least some embodiments, the mask value$_{i,j}$ corresponding to a pixel$_{i,j}$ having a satisfactory SNR is set to or otherwise defined as 1, and mask values corresponding to other pixels are set to or otherwise defined as 0.

See for example mask values in a region 1350 corresponding to pixels having a satisfactory SNR and set to 1, and mask values in a region 1352 corresponding to other pixels and set to 0.

As stated above, in at least some embodiments, the SNR mask 1302 is cumulative, meaning that if a pixel is masked as having unsatisfactory SNR at a given dynamic, it will remain masked as such throughout the treatment. Thus, in at least some embodiments, the SNR mask 1302 used in a given dynamic will be based at least in part on the SNR mask 1302 used in the prior dynamic. In at least some embodiments, a SNR mask 1302 for a given dynamic is made cumulative by determining the SNR mask 1302 as described above and multiplying it by the SNR mask 1302 used in the prior dynamic.

In at least some embodiments, each pixel identified as having unsatisfactory SNR will have its pixel values replaced and/or ignored. If it is to be replaced, it may be replaced with an estimated pixel value determined by linear or other interpolation based at least in part on the values of the four neighboring pixels (up, down, left, right) of the pixel.

As stated above, at least some aspects disclosed herein employ one or more dynamic correction methodologies during thermal treatment or other procedure.

FIG. 14. is a table 1400 that shows five different types of dynamic corrections that may be employed, characteristics thereof and representations of examples thereof (reduced in size compared to the size of the visualizations in FIG. 5A-5B), in accordance with at least some embodiments.

Referring to FIG. 14, these five different types of dynamic corrections are: drift correction, phase unwrap, temperature corrections, spatial co-registration and boing detection shut-off.

Drift correction is used to compensate, at least in part, for drift in the Larmor frequency of the MRI scanner, and thereby reduce the effects thereof, at least in part. During thermal treatment, the Larmor frequency of the MRI scanner may drift over time. As a consequence, the measured phase values, which are expected to be constant on unheated regions, may drift over time, which appears as temperature increase (sometimes referred to herein as artificial heating).

FIG. 15 is a flowchart of a method for drift correction to compensate, at least in part, for drift in the Larmor frequency of the MRI scanner over time, and thereby reduce the effects thereof, at least in part, in accordance with at least some embodiments.

Referring to FIG. 15, at 1502, the method includes determining a drift correction mask for each slice (e.g., 12 slices) in a current dynamic. In at least some embodiments, the mask for each slice may be determined by combining the following masks: (i) the thermal (ultrasound or otherwise) applicator mask, (ii) the rectum (or other restricted region) mask, (iii) the stability mask for the slice and (iv) the SNR mask for the slice as follows:

combinedMask=$UA$Mask×RectumMask×StabilityMask×SNRMask

At 1504, the method may further include, for each slice of the current dynamic, applying the combined mask for the slice to the phase difference image for the slice. In at least some embodiments, the combined mask for a slice may be applied to the phase difference image for the slice using pixel by pixel multiplication as follows:

$\Phi_{masked}(x,y,s) = \Phi(x,y,s) \times \text{combinedMask}(x,y,s)$

At 1506, the method may further include, for each slice of the current dynamic, determining a geometric fit or other approximation (sometimes referred to herein as an estimation or estimate) based at least in part on the masked phase difference image for the slice. In at least some embodiments, the geometric fit will be a plane fit or a parabola fit, depending on a correction order (sometimes referred to herein as an order of correction) that may be needed and/or chosen, which in at least some embodiment may be based at least in part on the type of scanner being used. For instance, if a second-order correction is to be used, an estimate $\hat{\Phi}$ based on $\Phi_{masked}$ may be determined as follows:

$\hat{\Phi}(x,y,s) = \beta_1 + \beta_2 x + \beta_3 y + \beta_4 xy + \beta_4 x^2 + \beta_5 y^2 + \in$ where $\in$ is the observed error of the model. This forms a linear set of equations which may be written as:

$\hat{\Phi}_{masked} = X\vec{\beta} + \vec{\in}$ where $$X = \begin{bmatrix} 1 & x_1 & y_1 & x_1 y_1 & x_1^2 & y_1^2 \\ \vdots & \vdots & \vdots & \vdots & \vdots & \vdots \\ 1 & x_n & y_n & x_n y_n & x_n^2 & y_n^2 \end{bmatrix}$$

is the Vandermonde matrix.
The solution of these equations is given by:

$\vec{\beta} = (X^T X)^{-1} X^T \vec{\Phi}$

At 1508, the method may further include determining a corrected phase image based at least in part on a difference between the surface and a current phase image. In at least some embodiments, this may be performed by subtracting the surface to the current phase image as follows:

$\Phi_{corrected} = \Phi - \hat{\Phi}_{masked}$

FIG. 16A is a full-size visualization 1600 (compared to the size of the visualizations in FIG. 5A-5B) of the example of drift correction shown in FIG. 14, in accordance with at least some embodiments.

FIG. 16B is a visualization 1650 that is similar to the visualization 1600 except that: (i) the temperature information in the visualization 1650 has had thresholding applied thereto (as a result, each shade in the visualization 1650 corresponds to a wider temperature range than does each shade in the visualization 1600) and pixels have been inverted (lowest temperatures are shown in white, increasingly higher temperatures are shown in increasingly darker shades, highest temperatures are shown in black) to assist in the teaching herein, reproduction and allow use of reference lines to point to aspects without a need for color, (ii) a border 1660 has been added to identify the portion of the visualization 1650 that represents a surface of the patient's body (e.g., the surface of the patient's abdomen) in the visualization 1650, and (iii) borders have been added around portions of the visualization 1650 that are associated with a same temperature range (after thresholding).

In at least some embodiments, the visualization 1600 and/or the visualization 1650 may be displayed on a visual output device such as a computer monitor screen or other display.

Referring again to FIG. 14, a second type of dynamic correction that may be employed is sometimes referred to herein as phase unwrap. Phase values are bound to a range between −π(−180 degrees) and +π (+180 degrees). As a result, a change in temperature can result in what is sometimes referred to as "phase wrap".

FIG. 17 is a graphical representation 1700 of one type of a phase wrap, in accordance with at least some embodiments. In the representation, a first phase measurement 1702 has a first phase of −175 degrees representing a first temperature 1704. Because of phase wrap 1706, a second phase measurement 1708, representing a second temperature 1710 (which is relatively close to the first temperature 1704), has a second phase of +175 degrees (which is disproportionately greater than the first phase of −175). In at least some embodiments, it is desirable to detect and compensate for phase wrap. The process of determining whether phase unwrap has occurred, and if it has, compensating for such is sometimes referred to herein as "phase unwrap".

In at least some embodiments, the occurrence of phase wrap is detected based at least in part on the change that a pixel phase value has undergone between two successive dynamics. In some embodiments, a change of more than n (in either direction) in a pixel phase value is used as an indication that phase wrap has occurred, and if phase wrap has occurred, it is compensated for by applying an offset of +2π or −2π (depending on the direction of the change) in accordance with the following:

If $\begin{cases} \Phi(d) - \Phi(d-1) > \pi, & \Phi(d) = \Phi(d-1) - 2\pi \\ \Phi(d) - \Phi(d-1) < -\pi, & \Phi(d) = \Phi(d-1) + 2\pi \end{cases}$ where d is the dynamic number.

Referring still to FIG. 14, a third type of dynamic correction that may be employed is sometimes referred to herein as temperature corrections. In at least some embodiments, it may happen that due to noisy measurements, a pixel phase value will be incorrectly unwrapped, and as a result may take very high or very low temperature values, beyond normal physiological values or another expected range. To address the above, in at least some embodiments, temperature correction may be carried out as follows. For every pixel in the phase image, if phase unwrap causes the temperature value of the pixel to fall outside the range [0;120] ° C. (i.e., outside the normal physiological range), or outside some other expected range, the phase is not unwrapped. For the range of [0;120] ° C., this may be implemented as follows:

$$\text{If } \begin{cases} \Phi(d) > \Phi_{120°}, & \Phi(d) = \Phi(d) - 2\pi \\ \Phi(d) < \Phi_{0°}, & \Phi(d) = \Phi(d) + 2\pi \end{cases}$$

where $\phi_{120° C.}$ and $\phi_{0° C.}$ are the phase values corresponding to the temperatures of 120° C. and 0° C. respectively.

Effectively, the above ensures that all pixels in the temperature maps are bound within the range [0;120] ° C. In at least some embodiments, a range other than 0 to 120° C. may be employed.

Referring still to FIG. 14, a fourth type of dynamic correction that may be employed is sometimes referred to herein as spatial co-registration (or image shift correction). If the amount of MRI scanner drift is significant over the course of the treatment, it is necessary (or at least desirable) to perform spatial co-registration between the received dynamics and the reference image, taken at the beginning of the treatment.

FIG. 18 is a representation 1800 showing a current image 1802 and a corresponding reference image 1804 prior to any spatial drift, and an alternative current image 1812 as a result of spatial drift 1814, in accordance with some embodiments.

Therefore, in at least some embodiments, the amount of spatial drift between the current dynamic and the reference image is determined every Y dynamics (or if not periodically, at least from time to time).

The amount of spatial drift may be determined by calculating or otherwise determining a measure of similarity between the current dynamic and the reference image, which may be determined by calculating or otherwise determining a cross-correlation between a Fourier-transform of the current dynamic and a Fourier-transform of the reference image. In at least some embodiments, the result of the cross-correlation is an image that contains a peak, the location of which is equal to or otherwise defines the amount of spatial shift between the two images. If the amount of the spatial shift is greater than 0.1 pixel (or other chosen threshold), it is necessary (or at least desirable) to spatially register the current dynamic and the reference image. If the amount of spatial shift is less than 1 pixel, spatially registering the current dynamic and the reference image will require interpolation.

In accordance with at least some embodiments, two approaches are possible: either align the reference image onto the current image, or align the current image onto the reference image. The former solution will require shifting the UA center too, and therefore the structural masks will have to be generated again.

FIG. 18 shows (a) a compensated reference image 1824 after compensation 1826 thereto and a compensated current image 1822 as a result of the compensation to the reference image, corresponding to the first approach, and (b) a compensated current image 1832 as a result of compensation 1836 thereto without any change to the reference image 1804, corresponding to the second approach, in accordance with some embodiments.

FIG. 19 is a full-size visualization 1900 (compared to the size of the visualizations in FIG. 5A-5B) of the example of boiling detection shutoff shown in FIG. 14, in accordance with at least some embodiments.

Referring again to FIG. 14, a fifth type of dynamic correction that may be employed is sometimes referred to herein as boiling detection shutoff. In at least some embodiments, it is critical or at least desirable to correctly detect temperature approaching 100° C. in tissue. To address the above, at least some embodiments employ a boiling detection shutoff method and/or mechanism to reduce the risk of tissue boiling. In at least some embodiments, the method and/or mechanism are based at least in part on the sector mask discussed above, which as discussed above, the positioning of which may be primarily (or at least in part) a function of the current beam angle. In at least some embodiments, the method and/or mechanism shut off at least a portion of (or otherwise reduce) the power to the therapy applicator if at any time, any one or more pixels within the sector mask has a temperature that is greater than a threshold or satisfies other criteria. FIG. 19 shows an example of pixels within an example of a sector mask (i.e., an example of pixels within the polygon 1308 (FIG. 13A). In at least some embodiments, the threshold is selected as an indication that a boiling temperature is approached. In at least some embodiments, the threshold is a temperature chosen from a range of from 86° C. to 90° C. In at least some embodiments, the threshold is 86° C. In at least some embodiments, the threshold is adjustable during therapy. In at least some embodiments, the adjustable threshold is adjustable to any temperature in the range of from 86° C. to 90° C. In at least some embodiments, at least a portion the at least one element that is shut off includes one or more elements supplying energy to a region of the patient associated with the one or more pixels that are within the sector mask and have a temperature that is greater than the threshold or satisfies the other criteria. In at least some embodiments, power to the therapy applicator is reduced by shutting off power to one, some or all elements of the therapy applicator that supply energy to a region of the patient associated with the one or more pixels that are within the sector mask and have a temperature that is greater than the threshold or satisfies the other criteria.

Thus, at least some aspects disclosed herein further reduce the effects of errors and/or potential errors in systems and methods that use temperature measurements derived from MRI.

Accordingly, improved accuracy and/or efficiency of delivery of MRI-guided thermal therapies and/or other systems and methods is made possible.

In at least some embodiments, one or more portions of any method (or system) disclosed herein may be used without one or more other portions of such method (or system).

In accordance with at least some embodiments, any one or more of the embodiments (or feature(s) thereof) disclosed herein may be used in association with any other embodiment(s) (or feature(s)) disclosed herein.

FIG. 20 is a flowchart of a method 2000 that employs a plurality of the methods disclosed herein or portion(s)

thereof and may be employed in delivery of therapy, in accordance with at least some embodiments.

In at least some embodiments, one or more portions of the method may be used in performing dynamic correction(s). In at least some embodiments, the dynamic correction(s) may improve accuracy and/or reduce uncertainty.

The method is not limited to the order shown, but rather may be performed in any practicable order. For that matter, any method disclosed herein is not limited to any particular order but rather may be performed in any practicable order.

In at least some embodiments, the method (or one or more portion(s) thereof) may be performed using one or more portions of one or more other methods disclosed herein. For that matter, in at least some embodiments, any method (or one or more portions thereof) disclosed herein may be performed using one or more portions of one or more other methods disclosed herein.

In at least some embodiments, the method (or one or more portion(s) thereof) may be performed in performance of one or more portions of one or more other methods disclosed herein. For that matter, in at least some embodiments, any method (or one or more portions thereof) disclosed herein may be performed in performance of one or more portions of one or more other methods disclosed herein.

In at least some embodiments, the method (or one or more portion(s) thereof) may be performed by system controller 200 (FIGS. 1-2).

Referring to FIG. 20, at 2002, the method may include receiving data indicative of at least one phase image captured using a magnetic resonance imaging (MRI) device during delivery of thermal therapy by a thermal therapy applicator to a target volume within a patient's body.

In at least some embodiments, the data may have any form(s) and may be received from any source(s) (internal and/or external).

In at least some embodiments the thermal therapy comprises ultrasound thermal therapy and the thermal therapy applicator comprises an ultrasound thermal therapy applicator.

At 2004, the method may further include applying a first mask.

In at least some embodiments, the first mask may comprise any mask, or any combination of masks, disclosed below or otherwise herein.

At 2006, the method may further include applying phase unwrap.

At 2008, the method may further include applying a second mask.

In at least some embodiments, the second mask may comprise any mask, or any combination of masks, disclosed below or otherwise herein.

In some embodiments, the first mask and the second mask may be combined with one another into a combined mask that is subsequently applied such that the first mask and second mask are applied at the same time as one another.

In accordance with at least some embodiments, the first mask, phase unwrap and the second mask may be applied in any suitable order. Thus, in at least some embodiments, the applying of the phase unwrap may be between the applying of the first mask and the applying of the second mask. In at least some embodiments, this may comprise applying the first mask to a first phase image to generate a first result image, applying the phase unwrap to the first result image to generate a second result image, and applying the second mask to the second result image to generate a third result image. In at least some embodiments, intermediate processing need not be excluded. Thus, in at least some embodiments, the applying of the phase unwrap between the applying of the first mask and the applying of the second mask may comprise: applying the first mask to a phase image to generate a first result image, applying the phase unwrap to a phase image that is based at least in part on the first result image to generate a second result image, and applying the second mask to a phase image that is based at least in part on the second result to generate a third result image.

In at least some embodiments, the applying of the phase unwrap may be prior to the applying of the first mask and the applying of the second mask. In at least some embodiments, the applying of the phase unwrap may be after the applying of the first mask and the applying of the second mask. As indicated above, in at least some embodiments, intermediate processing need not be excluded.

The method may further include determining a treatment plan after processing the at least one phase image.

The method may further include delivering thermal therapy to the target volume within the patient's body based at least in part on said treatment plan using a thermal therapy applicator.

FIGS. 21A-21D are a flowchart 2100 of another method that employs a plurality of the methods disclosed herein or portion(s) thereof and may be employed in delivery of therapy, in accordance with at least some embodiments.

In at least some embodiments, the method reduces the effects of errors and/or potential errors in MRI guided thermal therapy.

In at least some embodiments, one or more portions of the method may be used in performing dynamic correction(s). In at least some embodiments, the dynamic correction(s) may improve accuracy and/or reduce uncertainty.

Accordingly, improved accuracy and/or efficiency of delivery of MRI-guided thermal therapies is made possible.

As stated above, in at least some embodiments, one or more portions of any method (or system) disclosed herein may be used without one or more other portions of such method (or system).

In at least some embodiments, references below to static masks, dynamic masks, temperature uncertainty masks, structural masks, ultrasound applicator masks, rectum masks, prostate masks, sector masks, noise masks, SNR mask, stability mask, drift correction, phase unwrap, temperature corrections, spatial co-registration (image shift correction), boiling detection and/or boiling detection shutoff (and so on) refer to the static masks, dynamic masks, temperature uncertainty masks, structural masks, ultrasound applicator masks, rectum masks, prostate masks, sector masks, noise masks, SNR mask, stability mask, drift correction, phase unwrap, temperature corrections, spatial co-registration (image shift correction), boiling detection and/or boiling detection shutoff (and so on), respectively, described above with respect to FIGS. 1-20.

In at least some embodiments, the method (or one or more portion(s) thereof) may be performed by system controller 200 (FIGS. 1-2).

Referring now to FIGS. 21A-21D, at 2102, the method may include receiving information associated with a new patient 2102, calculating a pre-treatment TU map 2104, identifying any pixels that are within the prostate (or other region) and have a standard deviation greater than 2° C. (or other threshold or other criteria) 2106, and storing a TU mask generated based at least in part on the results thereof 2108.

The method further includes starting treatment 2110, calculating structural masks (i.e., UA mask, rectum mask and prostate mask and/or other structure mask(s))) 2112, storing the structural masks 2114, receiving a new dynamic 2116 and determining whether more than 5 dynamics have been received 2118.

If at 2118 it is determined that more than 5 dynamics have not been received, the method returns to 2116. Otherwise, the method proceeds to calculate a reference phase image 2120, store the reference phase image as a reference phase 2122 and determine whether a current dynamic is a multiple of 100 at 2124.

If at 2124 it is determined that the current dynamic is not a multiple of 100, the method proceeds to calculate phase difference between a current phase image and the reference plane 2126. Otherwise, the method stores the next 5 dynamics 2128, evaluate image shift 2130 and determine if the image shift is more than 0.1 pixel 2132.

If at 2132 it is determined that the image shift is more than 0.1 pixel, the method returns to 2124. Otherwise, the method proceeds to apply special co-registration 2134, recalculate structural masks 2136, and calculate phase difference between a current phase image and the reference plane 2126.

After calculating the phase difference between a current phase image and the reference plane at 2126, the method proceeds to apply phase unwrap 2138, identify pixels with low magnitude SNR 2140, and storing a SNR mask generated based at least in part on the results thereof 2142.

The method further includes identifying pixels whose temperature changed by greater than 10° C. (or other threshold or other criteria) between two dynamics, storing a stability mask generated based at least in part on the results thereof 2146, multiplying current SNR and stability masks with previous SNR and stability masks 2148, applying drift correction to masked phase images (UA & rectum & SNR and stability) 2150, applying phase unwrap 2152, applying temperature correction 2154, converting phase to temperature 2156, calculating sector mask based on current beam angle 2158, and storing a sector mask generated based at least in part on the results thereof 2160.

The method further includes determining whether any pixels are within the sector mask and above a threshold indicating that the temperature is approaching a boing temperature (or other temperature reference) 2162. If at 2162 it is determined that no pixels are within the sector mask and above a threshold indicating that the temperature is approaching a boing temperature (or other temperature reference), the method proceeds to apply controller decisions 2164. Otherwise, the method shuts off the element 2166 and then proceeds to apply controller decisions at 2164. Execution may then return to 2116.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

FIG. 22 is a block diagram of a computer architecture 2200 according to some embodiments. In some embodiments, one or more of the systems (or portion(s) thereof), apparatus (or portion(s) thereof) and/or devices (or portion(s) thereof) disclosed herein may have an architecture that is the same as and/or similar to one or more portions of the architecture 2200.

In some embodiments, one or more of the methods (or portion(s) thereof) disclosed herein may be performed by a system, apparatus and/or device having an architecture that is the same as or similar to the architecture 2200 (or portion(s) thereof). The architecture may be implemented as a distributed architecture or a non-distributed architecture.

Referring to FIG. 22, in accordance with at least some embodiments, the architecture 2200 may include one or more processors 2210 and one or more articles of manufacture that comprise non-transitory computer-readable storage media (e.g., memory 2220 and one or more non-volatile storage media 2230). The processor 2210 may control writing data to and reading data from the memory 2220 and the non-volatile storage device 2230 in any suitable manner, as the aspects of the disclosure provided herein are not limited in this respect. The storage media may store one or more programs and/or other information for operation of the architecture 2200. In at least some embodiments, the one or more programs include one or more instructions to be executed by the processor 2210 to provide one or more portions of one or more tasks and/or one or more portions of one or more methods disclosed herein. In some embodiments, other information includes data for one or more portions of one or more tasks and/or one or more portions of one or more methods disclosed herein. To perform any of the functionality described herein, the processor 2210 may execute one or more processor-executable instructions stored in one or more non-transitory computer-readable storage media (e.g., the memory 2220), which may serve as non-transitory computer-readable storage media storing processor-executable instructions for execution by the processor 2210.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more communication devices 2240, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices 2250 and/or one or more output devices 2260. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

It should be understood that the features disclosed herein can be used in any combination or configuration. Thus, for example, in some embodiments, any one or more of the features disclosed herein may be used without any one or more other feature disclosed herein.

Unless stated otherwise, a computing device is any type of device that includes at least one processor.

Unless stated otherwise, a processing device is any type of device that includes at least one processor.

Unless stated otherwise, a processing system is any type of system that includes at least one processor.

Unless stated otherwise, a mobile (or portable) computing device includes, but is not limited to, any computing device that may be carried in one or two hands and/or worn.

Unless stated otherwise, a processor may comprise any type of processor. For example, a processor may be programmable or non-programmable, general purpose or special purpose, dedicated or non-dedicated, distributed or non-distributed, shared or not shared, and/or any combination thereof. A processor may include, but is not limited to, hardware, software (e.g., low-level language code, high-level language code, microcode), firmware, and/or any combination thereof.

Unless stated otherwise, a program may include, but is not limited to, instructions in a high-level language, low-level language, machine language and/or other type of language or combination thereof.

Unless stated otherwise, a "communication link" may comprise any type(s) of communication link(s), for example, but not limited to, wired links (e.g., conductors, fiber optic cables) or wireless links (e.g., acoustic links, radio links, microwave links, satellite links, infrared links or other electromagnetic links) or any combination thereof, each of which may be public and/or private, dedicated and/or shared. In some embodiments, a communication link may employ a protocol or combination of protocols including, for example, but not limited to the Internet Protocol.

Unless stated otherwise, information may include data and/or any other type of information.

Unless stated otherwise, terms such as, for example, "in response to" and "based on" mean "in response (directly and/or indirectly) at least to" and "based (directly and/or indirectly) at least on", respectively, so as not to preclude intermediates and being responsive to and/or based on, more than one thing.

Unless stated otherwise, the term "represents" means "directly represents" and/or "indirectly represents."

Unless stated otherwise, terms such as, for example, "comprises," "has," "includes," and all forms thereof, are considered open-ended, so as not to preclude additional elements and/or features.

Also, unless stated otherwise, terms such as, for example, "a," "one," "first," are considered open-ended, and do not mean "only a", "only one" or "only a first", respectively. Also, unless stated otherwise, the term "first" does not, by itself, require that there also be a "second."

Also, unless stated otherwise, the phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method comprising:
    receiving phase data indicative of at least one phase image captured using a magnetic resonance imaging (MRI) device during delivery of thermal therapy by a thermal therapy applicator to a target volume within a patient's body; and
    processing said at least one phase image;
    wherein said processing said at least one phase image comprises:
        applying a first mask to the phase data;
        applying phase unwrap;
        determining that a temperature represented by a phase value of a pixel would be outside an expected range if said phase value of said pixel is unwrapped;
        in response to said determining that a temperature represented by said phase value of a pixel would be outside an expected range if said phase value of said pixel is unwrapped, not unwrapping said phase value of said pixel; and
        applying a second mask to the phase data,
    wherein said first mask or said second mask comprises a dynamic mask and wherein said dynamic mask comprises a sector mask;
    wherein the thermal therapy applicator rotates during delivery of the thermal therapy;
    wherein the thermal therapy applicator emits a thermal therapy beam;
    wherein the sector mask is a boiling detection mask that includes pixels within a polygon that receives energy from the therapy applicator and has: (i) a first side defined by a thermal therapy target region boundary, (ii) a second side having a defined positional relation to the thermal therapy applicator and (iii) third and fourth sides defined by lines disposed on opposite sides of, and angularly displaced from, a current therapy beam centerline extending from the therapy applicator in a direction at which a center of the thermal therapy beam is emitted at a current point in time.

2. The method of claim 1 further comprising:
    determining a treatment plan based at least in part on the processed at least one phase image; and
    delivering thermal therapy to the target volume within the patient's body based at least in part on said treatment plan using the thermal therapy applicator.

3. The method of claim 1 wherein said applying phase unwrap comprises:
    applying said phase unwrap between said applying a first mask and said applying a second mask.

4. The method of claim 1 wherein said thermal therapy comprises ultrasound thermal therapy; and
    wherein said thermal therapy applicator comprises an ultrasound thermal therapy applicator.

5. The method of claim 1 wherein said first mask is a static mask and said second mask is a dynamic mask.

6. The method of claim 1 wherein:
    said first mask comprises a therapy applicator mask that excludes pixels within a predetermined distance from a center of the thermal therapy applicator, and
    said second mask comprises the sector mask.

7. The method of claim 6 wherein said therapy applicator mask is an ultrasonic applicator mask that excludes pixels within a predetermined distance from a center of an ultrasonic therapy applicator.

8. The method of claim 1 wherein:
    said first mask comprises a target region mask, and
    said second mask comprises the sector mask.

9. The method of claim 8 wherein said target region mask is a prostate mask that only includes pixels within a contour of the patient's prostate.

10. The method of claim 1 wherein:
    said first mask comprises a restricted region mask that excludes pixels within a region offset from a center of the thermal therapy applicator, and
    said second mask comprises the sector mask.

11. The method of claim 10 wherein said restricted region mask is a rectum mask.

12. The method of claim 1 wherein:
    said first mask comprises a dynamic mask and wherein said dynamic mask comprises a noise mask that excludes pixels that exceed a noise threshold during the delivery of the thermal therapy, and
    said second mask comprises the sector mask.

13. The method of claim 1 wherein said first mask and/or said second mask comprises a plurality of values arranged in an array having a plurality of rows and a plurality of columns, each of the plurality of values having a location in the array corresponding to a location in one or more MRI images.

14. The method of claim 1, wherein the dynamic mask is a first dynamic mask and the sector mask is a first sector mask,
wherein the second mask comprises the sector mask, and
wherein the first mask comprises a second dynamic mask,
wherein the second dynamic mask comprises a second sector mask that is dynamically generated based at least in part on a current beam angle of the thermal therapy applicator with respect to the phase image, and wherein said processing said at least one phase image further comprises
determining the temperature of each pixel based on a phase difference between a current phase of each pixel in the phase image and a reference phase of a corresponding pixel in a reference image; and
adjusting a power to the thermal therapy applicator when the temperature of any pixel within the second sector mask is greater than a threshold temperature.

15. The method of claim 1 wherein the second side of the polygon is defined by a circle having a center at a center of the therapy applicator.

16. The method of claim 1 wherein the thermal therapy applicator rotates about its axis during delivery of the thermal therapy so as to sweep through a treatment volume defined by a treatment boundary; and the second side of the polygon is defined by a circle having a center at a center of the therapy applicator.

17. A system comprising:
at least one computer hardware processor configured to perform:
receiving phase data indicative of at least one phase image captured using a magnetic resonance imaging (MRI) device during delivery of thermal therapy by a thermal therapy applicator to a target volume within a patient's body; and
processing said at least one phase image;
wherein said processing said at least one phase image comprises:
applying a first mask to the phase data;
applying phase unwrap;
determining that a temperature represented by a phase value of a pixel would be outside an expected range if said phase value of said pixel is unwrapped;
in response to said determining that a temperature represented by said phase value of a pixel would be outside an expected range if said phase value of said pixel is unwrapped, not unwrapping said phase value of said pixel; and
applying a second mask to the phase data,
wherein said first mask or said second mask comprises a dynamic mask and wherein said dynamic mask comprises a sector mask;
wherein the thermal therapy applicator rotates during delivery of the thermal therapy;
wherein the thermal therapy applicator emits a thermal therapy beam;
wherein the sector mask is a boiling detection mask that includes pixels within a polygon that receives energy from the therapy applicator and has: (i) a first side defined by a thermal therapy target region boundary, (ii) a second side having a defined positional relation to the thermal therapy applicator and (iii) third and fourth sides defined by lines disposed on opposite sides of, and angularly displaced from, a current therapy beam centerline extending from the therapy applicator in a direction at which a center of the thermal therapy beam is emitted at a current point in time.

18. The system of claim 17 wherein the at least one computer hardware processor is further configured to perform:
determining a treatment plan based at least in part on the processed at least one phase image; and
delivering thermal therapy to the target volume within the patient's body based at least in part on said treatment plan using the thermal therapy applicator.

19. The system of claim 17 wherein said applying phase unwrap comprises:
applying said phase unwrap between said applying a first mask and said applying a second mask.

20. At least one non-transitory computer readable storage medium storing processor-executable instructions that, when executed by at least one processor, result in a method comprising:
receiving phase data indicative of at least one phase image captured using a magnetic resonance imaging (MRI) device during delivery of thermal therapy by a thermal therapy applicator to a target volume within a patient's body; and
processing said at least one phase image;
wherein said processing said at least one phase image comprises:
applying a first mask to the phase data;
applying phase unwrap;
determining that a temperature represented by a phase value of a pixel would be outside an expected range if said phase value of said pixel is unwrapped;
in response to said determining that a temperature represented by said phase value of a pixel would be outside an expected range if said phase value of said pixel is unwrapped, not unwrapping said phase value of said pixel; and applying a second mask to the phase data,
wherein said first mask or said second mask comprises a dynamic mask and wherein said dynamic mask comprises a sector mask;
wherein the thermal therapy applicator rotates during delivery of the thermal therapy;
wherein the thermal therapy applicator emits a thermal therapy beam;
wherein the sector mask is a boiling detection mask that includes pixels within a polygon that receives energy from the therapy applicator and has: (i) a first side defined by a thermal therapy target region boundary, (ii) a second side having a defined positional relation to the thermal therapy applicator and (iii) third and fourth sides defined by lines disposed on opposite sides of, and angularly displaced from, a current therapy beam centerline extending from the therapy applicator in a direction at which a center of the thermal therapy beam is emitted at a current point in time.

21. The at least one medium of claim 20, wherein the method further comprises:
determining a treatment plan based at least in part on the processed at least one phase image; and
delivering thermal therapy to the target volume within the patient's body based at least in part on said treatment plan using the thermal therapy applicator.

22. The at least one medium of claim 20, wherein said applying phase unwrap comprises:

applying said phase unwrap between said applying a first mask and said applying a second mask.

\* \* \* \* \*